United States Patent
Oza et al.

(10) Patent No.: US 12,364,802 B2
(45) Date of Patent: *Jul. 22, 2025

(54) SYSTEMS AND METHODS FOR MECHANICAL DISPLACEMENT OF AN ESOPHAGUS

(71) Applicant: Ohio State Innovation Foundation, Columbus, OH (US)

(72) Inventors: Veeral M. Oza, Chicago, IL (US); Adam Hensel, Gahanna, OH (US); Emile Daoud, Columbus, OH (US); Nishaki Mehta, Boston, MA (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,902

(22) Filed: Dec. 20, 2023

(65) Prior Publication Data
US 2024/0197979 A1    Jun. 20, 2024

Related U.S. Application Data

(63) Continuation of application No. 17/739,721, filed on May 9, 2022, now Pat. No. 11,890,406, which is a
(Continued)

(51) Int. Cl.
*A61M 1/00*      (2006.01)
*A61B 1/015*     (2006.01)
(Continued)

(52) U.S. Cl.
CPC ............... *A61M 1/80* (2021.05); *A61B 1/015* (2013.01); *A61B 1/2733* (2013.01); *A61B 5/061* (2013.01);
(Continued)

(58) Field of Classification Search
CPC .......... A61B 2018/00488; A61B 2018/00577; A61B 18/1492; A61B 17/1114;
(Continued)

(56) References Cited

U.S. PATENT DOCUMENTS 3,799,151 A    3/1974  Fukaumi et al.
4,304,239 A   12/1981  Perlin
(Continued)

FOREIGN PATENT DOCUMENTS

CN    104640509    5/2015
CN    104688346    6/2015
(Continued)

OTHER PUBLICATIONS

International Search Report and Written Opinion dated May 10, 2018, in connection with International Application No. PCT/US2018/014467.
(Continued)

*Primary Examiner* — Marcela I. Shirsat
(74) *Attorney, Agent, or Firm* — Meunier Carlin & Curfman LLC

(57) ABSTRACT

An example assembly for use with a vacuum system and an esophageal positioning device esophageal positioning device includes an introducer, in which the esophageal positioning device includes a handle, a first segment, a second segment and an articulation driving mechanism. The first segment being coupled to the handle. The second segment being pivotally connected to the first segment. The articulation driving mechanism being configured to pivot the second segment about the first segment upon articulation.

20 Claims, 35 Drawing Sheets

Related U.S. Application Data continuation of application No. 16/401,477, filed on May 2, 2019, now Pat. No. 11,324,874, which is a continuation of application No. 15/875,360, filed on Jan. 19, 2018, now Pat. No. 10,307,520.

(60) Provisional application No. 62/448,139, filed on Jan. 19, 2017.

(51) Int. Cl.
| | | |
|---|---|---|
| A61B 1/273 | (2006.01) | |
| A61B 5/00 | (2006.01) | |
| A61B 5/01 | (2006.01) | |
| A61B 5/06 | (2006.01) | |
| A61B 7/02 | (2006.01) | |
| A61B 17/02 | (2006.01) | |
| A61B 18/00 | (2006.01) | |
| A61B 18/14 | (2006.01) | |
| A61M 25/01 | (2006.01) | |

(52) U.S. Cl.
CPC .......... *A61B 5/4233* (2013.01); *A61B 5/0077* (2013.01); *A61B 5/01* (2013.01); *A61B 5/687* (2013.01); *A61B 7/023* (2013.01); *A61B 17/0218* (2013.01); *A61B 2018/00351* (2013.01); *A61B 2018/00488* (2013.01); *A61B 2018/00577* (2013.01); *A61B 2018/00791* (2013.01); *A61B 18/1492* (2013.01); *A61M 25/0147* (2013.01)

(58) Field of Classification Search
CPC ....... A61B 7/023; A61B 5/0421; A61B 5/687; A61B 5/4233; A61B 5/1492; A61B 1/2733; A61B 1/273; A61B 17/0218; A61M 1/0084; A61M 25/0147
USPC ......... 600/139–142, 144–150, 114, 116–118, 600/129, 159, 244, 136, 134, 121
See application file for complete search history.

(56) References Cited

U.S. PATENT DOCUMENTS

| | | | |
|---|---|---|---|
| 4,612,927 A | 9/1986 | Kruger | |
| 4,930,521 A | 6/1990 | Metzger et al. | |
| 5,170,803 A | 12/1992 | Hewson | |
| 5,467,763 A | 11/1995 | McMahon et al. | |
| 5,531,776 A | 7/1996 | Ward et al. | |
| 6,285,898 B1 | 9/2001 | Ben-Haim | |
| 6,296,654 B1 | 10/2001 | Ward | |
| 6,958,052 B1 | 10/2005 | Charlton | |
| 7,621,908 B2 | 11/2009 | Miller | |
| 7,779,845 B2 | 8/2010 | Ortiz | |
| 8,092,378 B2 | 1/2012 | Roth et al. | |
| 8,273,016 B2 | 9/2012 | O'Sullivan | |
| 8,454,588 B2 | 6/2013 | Rieker et al. | |
| 8,529,443 B2 | 9/2013 | Maloney | |
| 8,905,919 B2 | 12/2014 | Matsuo et al. | |
| 9,668,720 B2 | 6/2017 | Kasic, II | |
| 10,307,520 B2 * | 6/2019 | Oza ........................ | A61B 1/015 |
| 11,324,874 B2 | 5/2022 | Oza et al. | |
| 2004/0249239 A1 | 12/2004 | Silverman et al. | |
| 2005/0261673 A1 | 11/2005 | Bonner et al. | |
| 2007/0010782 A1 | 1/2007 | Doty et al. | |
| 2007/0118105 A1 | 5/2007 | Miller | |
| 2007/0135803 A1 * | 6/2007 | Belson ............... | A61B 1/00154 606/1 |
| 2007/0225701 A1 | 9/2007 | O'Sullivan | |
| 2007/0233161 A1 * | 10/2007 | Weller ................... | A61B 90/92 606/220 |
| 2008/0033415 A1 * | 2/2008 | Rieker ............... | A61M 25/0147 606/191 |
| 2009/0112248 A1 | 4/2009 | Maloney | |
| 2011/0282338 A1 | 11/2011 | Fojtik | |
| 2013/0310806 A1 | 11/2013 | Nevler et al. | |
| 2014/0188080 A1 | 7/2014 | Besser et al. | |
| 2015/0150575 A1 | 6/2015 | Hartoumbekis et al. | |
| 2015/0174013 A1 | 6/2015 | Besser et al. | |
| 2016/0158111 A1 | 6/2016 | Besser et al. | |
| 2016/0317138 A1 | 11/2016 | Kasic et al. | |
| 2017/0035273 A1 | 2/2017 | Yasunaga | |
| 2017/0105715 A1 * | 4/2017 | Kasic, II .......... | A61B 17/00234 |
| 2017/0143589 A1 | 5/2017 | Besser et al. | |
| 2017/0360503 A1 | 12/2017 | Miller | |

FOREIGN PATENT DOCUMENTS

| | | |
|---|---|---|
| CN | 106028969 | 10/2016 |
| JP | 2003/520068 | 12/2004 |
| JP | 2008/535556 | 9/2008 |
| WO | 01/12102 | 2/2001 |
| WO | 2006105283 | 10/2007 |
| WO | 2014/047245 | 3/2014 |
| WO | 2015/100000 | 7/2015 |
| WO | 2016/017388 | 2/2016 |
| WO | 2017049313 | 3/2017 |

OTHER PUBLICATIONS

Mossaab Shuraih et al., Strategies to Prevent Esophageal Injury During Catheter Ablation of Atrial Fibrillation, 3 The Journal of Innovations in Cardiac Rhythm Management, 719-726 (2012).
International Preliminary Report on Patentability issued by the International Bureau of WIPO in PCT Application No. PCT/US2018/014467 on Jan. 19, 2018. 9 pages.
European Search Report issued by the European Patent Office in Application No. 18741612.8 on Oct. 20, 2020. 7 pages.
Examination Report No. 1. AU Application No. 2018210381. Aug. 2, 2022. 4 pages.
Office Action in JP Application No. 2019-538664. Jul. 20, 2022. 7 pages including machine translation.
Office Action issued in EP Application No. 18741612.8 on Feb. 3, 2023. 4 pages.
Decision to Grant issued in JP Application No. 2019-538664 on Dec. 21, 2022. 5 pages including machine translation.
Office Action issued in Chinese Application No. 2023061700221660. Jun. 17, 2023. 8 pages.
Office Action issued in Israeli Application No. 298033. Aug. 10, 2023. 4 pages.
Office Action issued in Israeli Application No. 298033. Dec. 20, 2023. 4 pages.
Office Action issued in Australian Application No. 2018210381 on Jul. 6, 2023. 3 pages.
Notice of Acceptance issued in Australian Application No. 2018210381 on Aug. 18, 2023. 4 pages.
European Patent Office. Extended European Search Report. Issued in EP Application No. 23218023.2 on Apr. 30, 2024. 7 pages.
Canadian Intellectual Property Office. Office Action issued in CA Application No. 3,051,110 on Jun. 18, 2024. 5 pages.
Chinese National Intellectual Property Administration. Notice of Allowance issued in CN Application No. 201880015298.X on Jun. 26, 2024. 4 pages.

* cited by examiner

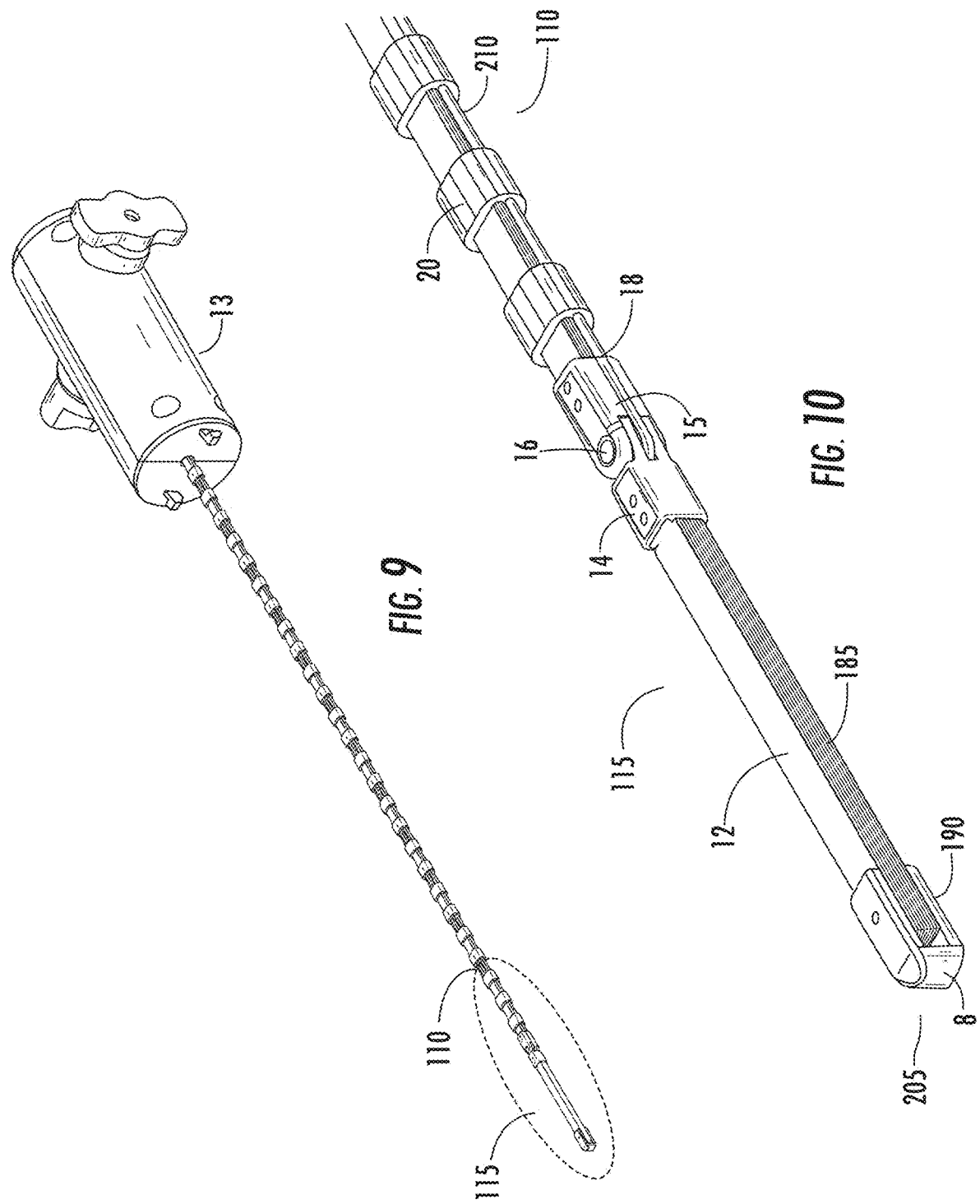

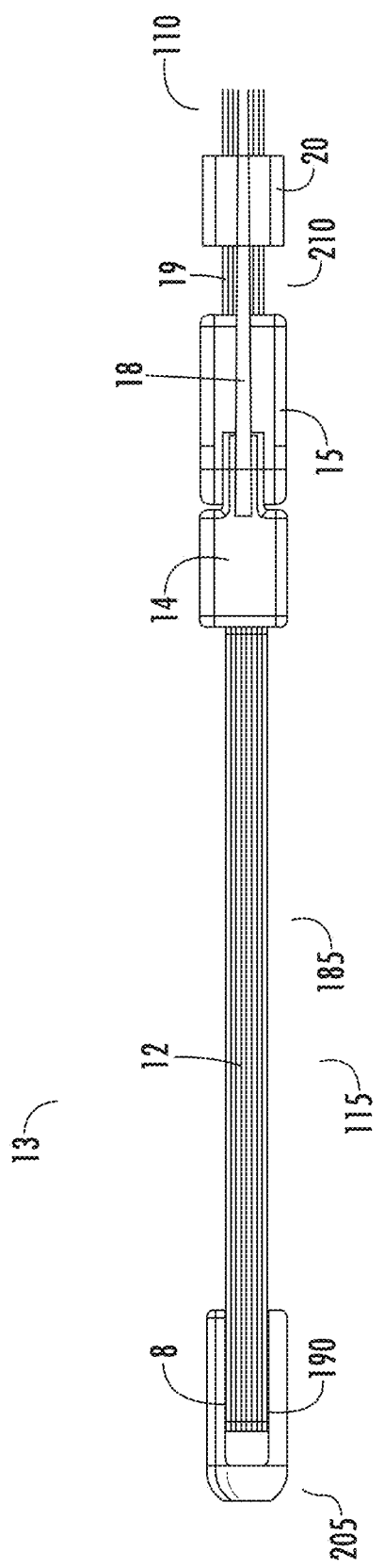
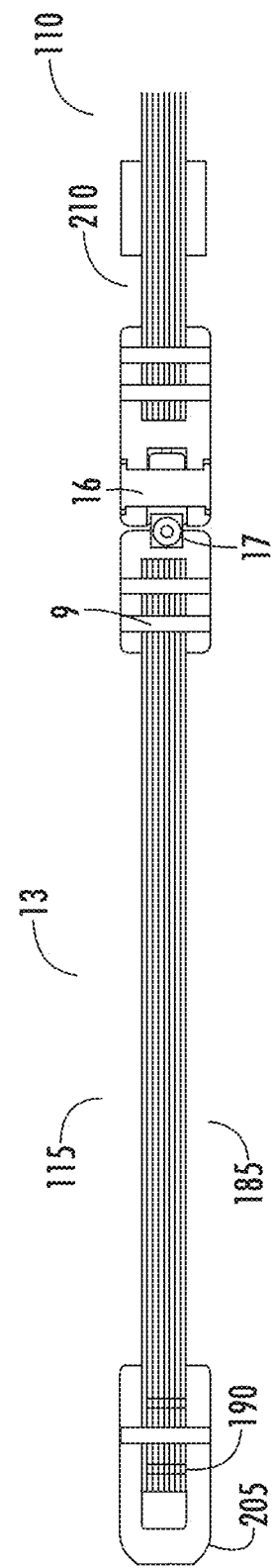
FIG. 11
FIG. 12

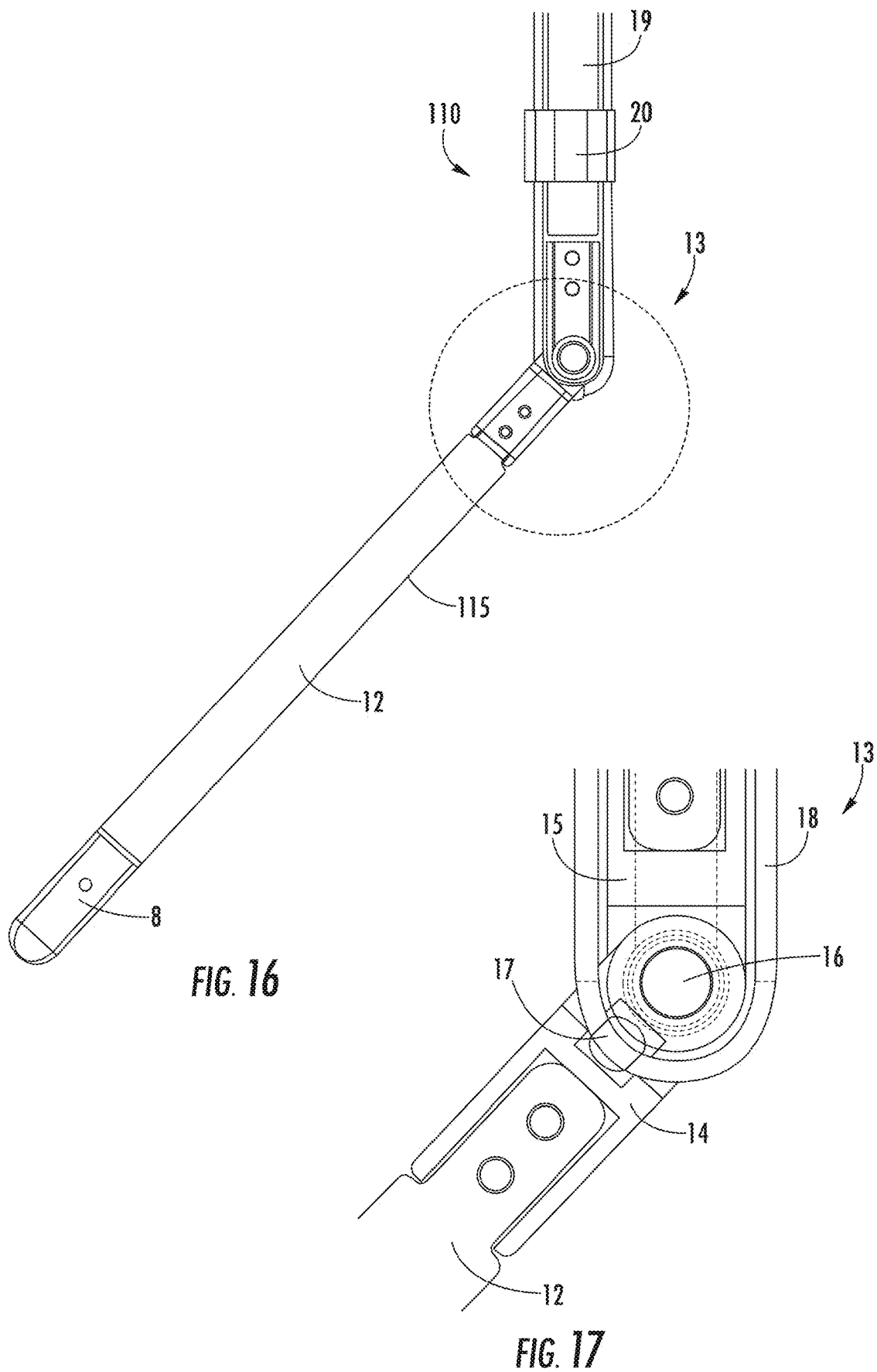

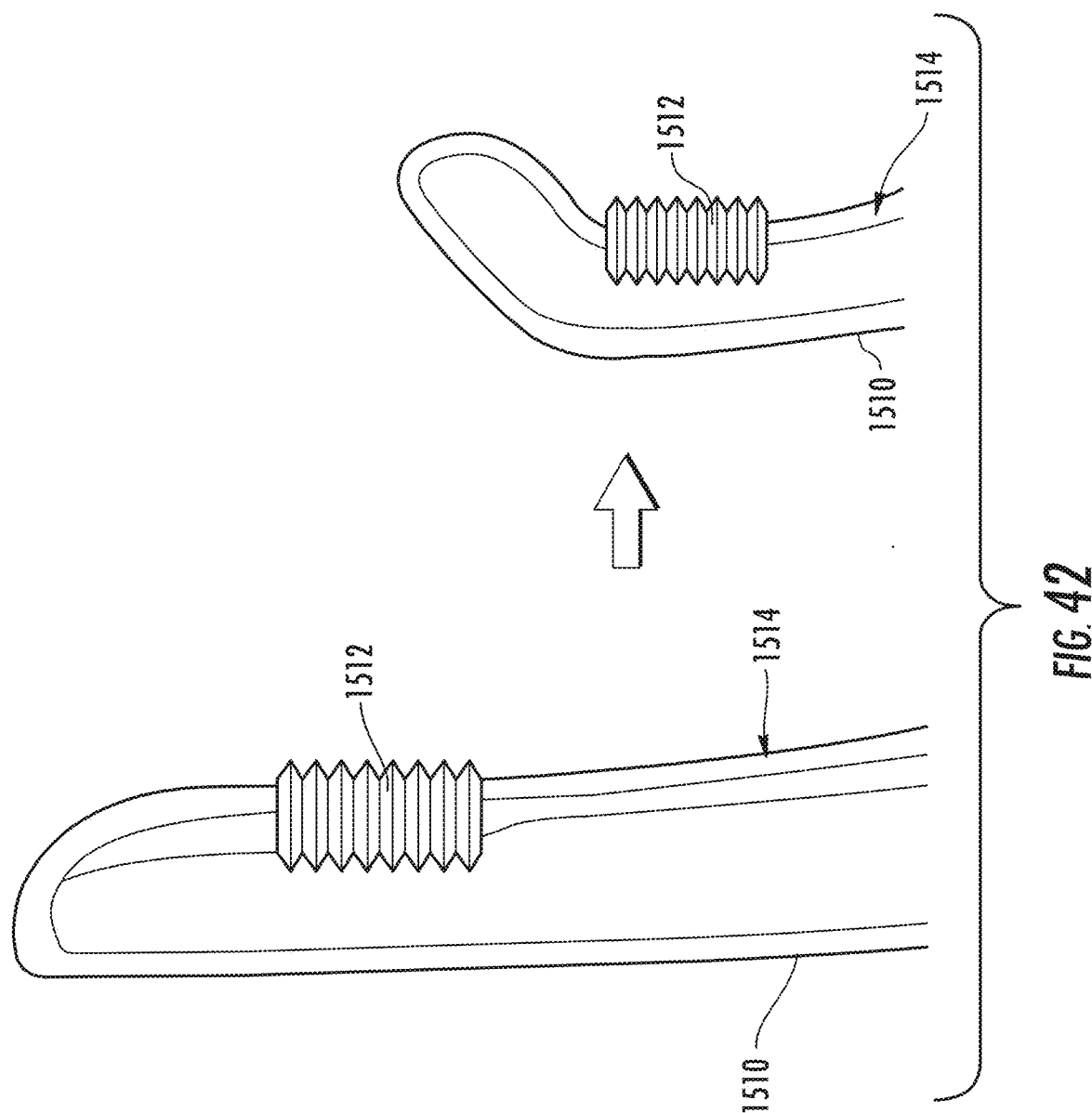

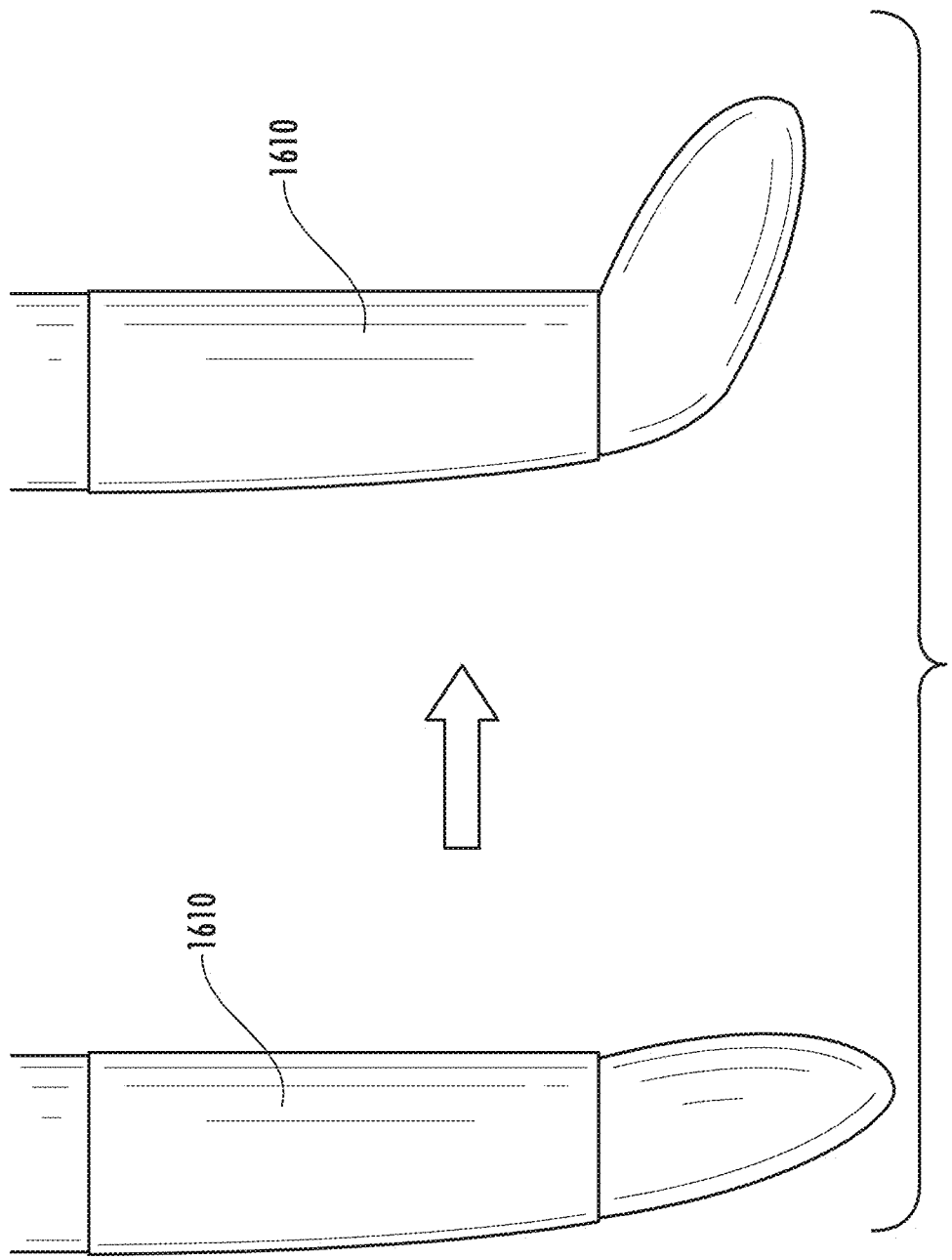

SYSTEMS AND METHODS FOR MECHANICAL DISPLACEMENT OF AN ESOPHAGUS

CROSS REFERENCE TO RELATED APPLICATIONS

This application is a continuation of U.S. patent application Ser. No. 17/739721, filed on May 9, 2022, which is a continuation of U.S. patent application Ser. No. 16/401477, filed on May 2, 2019, now U.S. Pat. No. 11324874, which is a continuation of U.S. patent application Ser. No. 15/875,360, filed Jan. 19, 2018, now U.S. Pat. No. 10307520, which claims the benefit of U.S. Provisional Patent Application No. 62/448,139, filed Jan. 19, 2017, the contents of which are herein incorporated by reference in their entirety.

TECHNICAL FIELD

This disclosure relates to medical devices and methods for vacuum suction adherence of the esophagus coupled with mechanical displacement of an esophagus of a patient.

BACKGROUND

It has been projected that, the number of patients experiencing atrial fibrillation ("AF") will increase to 10 million in 20 years. The cost of treating a patient with AF ranges from $2,000 U.S. to over $10,000 U.S. each year. The most effective and expanding method of treating AF is with a procedure called catheter ablation. Catheter ablation is designed to deliver energy (for example, radiofrequency and cryoenergy) through a catheter that is placed in the left atrium of the heart. The ablation results in destruction of the heart cells. The areas of the heart that are targeted for ablation are the areas that cause AF. These areas in the left atrium lie within 2-4 millimeters of the esophagus, thus a major concern is that energy from the ablation catheter can radiate forward and injure the esophagus. In the United States, approximately 103,000 AF ablation procedures are performed each year, and an additional 57,000 procedures are performed outside the U.S. A serious complication of an AF ablation procedure is injury to the esophagus that results in an atrial-esophageal fistula. This communication between the esophagus and the heart occurs because the ablation energy inflames the heart and the esophagus. The subsequent healing results in a hole/communication between the heart (a sterile organ) and the esophagus (not sterile organ). This communication may result in an infection of the heart and stroke. An atrial-esophageal fistula occurs in about 0.6% of patients and the outcome is nearly always fatal or associated with significant morbidity. Furthermore, the precursor to an atrial-esophageal fistula is ulcers in the esophagus, which are also due to injury of the esophagus and occurs in about 30% of patients. Hence electrophysiologists, physicians who perform the ablation procedure, are quite concerned about preventing damage to the esophagus and to avoid atrial-esophageal fistula.

Conventional therapy includes inserting a device into the esophagus to monitor temperature and to abort delivery of ablation energy once there is a change in luminal esophageal temperature. However, these devices are unable to displace the esophagus away from the energy source of the ablation and thus do not offer an active protective mechanism to guard against injury to the esophagus.

Therefore, improved systems for displacing an esophagus are needed so to reduce the risk of injury to the esophagus.

SUMMARY

Provided are devices, systems, and methods for vacuum suction adherence and mechanical displacement of an esophagus. In particular, disclosed are assemblies for use with a vacuum system and an esophageal positioning device. Disclosed as well are mechanical esophageal displacement systems, and methods of use.

The esophagus is a flexible muscular organ and is often moved during medical procedures. If mere mechanical force is applied to move the esophagus, tenting of the esophagus may result rather than actual movement and displacement of a region of the organ. More specifically, the mechanical force will displace the leading edge of the esophageal wall, but the trailing edge of the esophageal wall will move only a small distance, if any. The resulting tenting of the esophagus fails to provide protective benefit from the mechanical displacement. The systems disclose herein utilize suction vacuum to apply a uniform force to the esophagus to pull the esophageal wall in and adhere the esophageal walls in a circumferential manner. Under this physiologic condition, along with application of a mechanical force, the entire circumferential segment of the esophagus is displaced and there is no lagging or trailing edge of the esophagus. In general, the esophagus follows the directional changes of the esophageal positioning device via the assembly. This directional change can be easily visualized by the physician on the x-ray equipment via the use of radiopaque markers. The visualization provides immediate feedback to the physician. By moving the esophagus outside the ablation field, the AF procedure can proceed relatively safely without risk of damage to the esophagus, and the operator can ablate the targeted areas with confidence without concern for esophageal damage.

An example assembly includes an introducer for use with a vacuum system and an esophageal positioning device esophageal positioning device. The esophageal positioning device includes a handle, a first segment, a second segment, and an articulation driving mechanism. The first segment being coupled to the handle. The second segment being pivotally connected to the first segment. The articulation driving mechanism being configured to pivot the second segment about the first segment upon articulation. In some embodiments, the second segment is sized to displace the esophageal wall by about 4 centimeters upon articulation.

The introducer of the example assembly includes a soft cyclical outer tube, and a tube tip. The soft outer tube being sized to pass through a mouth or nasal passage into an esophagus, in which the soft outer tube includes a distal end, a proximal end, a lumen, and a body. The body of the outer tube includes a perforated outer surface, and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip is located at the distal end of the outer tube.

An example mechanical esophageal displacement system includes an assembly and an esophageal positioning device, in which the assembly is operatively coupleable to a vacuum system. The assembly comprises an introducer that includes a soft cyclical outer tube, and a tube tip. The soft outer tube being sized to pass through a mouth or nasal passage into an esophagus, in which the soft outer tube includes a distal end, a proximal end, a lumen, and a body. The body of the outer tube includes a perforated outer surface and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip being located at the distal end of the outer tube.

The esophageal positioning device of the example mechanical esophageal displacement system includes a handle, a first segment, a second segment, and an articulation driving mechanism. The first segment being coupled to the handle. The second segment being pivotally connected to the first segment. The articulation driving mechanism being configured to pivot the second segment about the first segment upon articulation.

An example method of using a mechanical esophageal displacement system includes inserting an assembly into an esophagus of a patient via a mouth or nasal passage. The assembly includes an introducer having a soft cyclical outer tube, a vacuum port, and a tube tip. The soft outer tube being sized to pass through a mouth or nasal passage into an esophagus, in which the soft outer tube includes a distal end, a proximal end, a lumen, and a body. The body of the outer tube includes a perforated outer surface and one or more internal vacuum passages that extend a distance from the proximal end towards the distal end within the body of the outer tube. In some embodiments, the perforated outer surface includes a plurality of vacuum holes spaced circumferentially around, and extending radially from, the soft outer tube. Because the plurality of vacuum holes are spaced circumferentially around the soft outer tube, the plurality of vacuum holes are located on multiple sides of the tube and can suction the esophagus from multiple directions. The one or more internal vacuum passages are in fluid communication with the plurality of vacuum holes to apply a vacuum to an esophageal wall via the vacuum system. The tube tip being located at the distal end of the outer tube. The vacuum port includes a vacuum port body, a vacuum line hook up, and a vacuum port cap.

The example method further includes advancing an esophageal positioning device through the outer tube of the introducer, in which the esophageal positioning device includes a handle, a first segment, a second segment, and an articulation driving mechanism. The first segment being coupled to the handle. The second segment being pivotally connected to the first segment. The articulation driving mechanism being configured to pivot the second segment about the first segment upon articulation.

The example method further includes snapping the handle of the esophageal positioning device to the vacuum port cap of the introducer, engaging the vacuum system to adhere a portion of the outer tube to an esophageal wall, and articulating the articulation driving mechanism to pivot the second segment about the first segment to a selected angle.

The details of one or more embodiments of the disclosure are set forth in the accompanying drawings and the description below. Other features, objects, and advantages of the disclosure will be apparent from the description, drawings, and from the claims.

DESCRIPTION OF DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein:

FIG. 9 is perspective view of an example esophageal positioning device of the mechanical esophageal displacement system of FIG. 1;

FIG. 10 is a perspective, zoomed in view, of a portion of the esophageal positioning device of FIG. 9;

FIG. 11 is a side view of the portion of the esophageal positioning device of FIG. 10;

FIG. 12 is a top view of the portion of the esophageal positioning device of FIG. 10;

FIG. 16 shows a top view of a portion of the mechanical esophageal displacement system of FIG. 1, in which the view shows an esophageal positioning device being positioned in a first angular orientation;

FIG. 17 is a top, zoomed in, view of the portion of the esophageal positioning device of FIG. 16;

FIG. 42 is a perspective view of another example assembly in accordance with the present disclosure; and FIG. 43 is a perspective view of another example assembly in accordance with the present disclosure.

DETAILED DESCRIPTION

Figure 1:
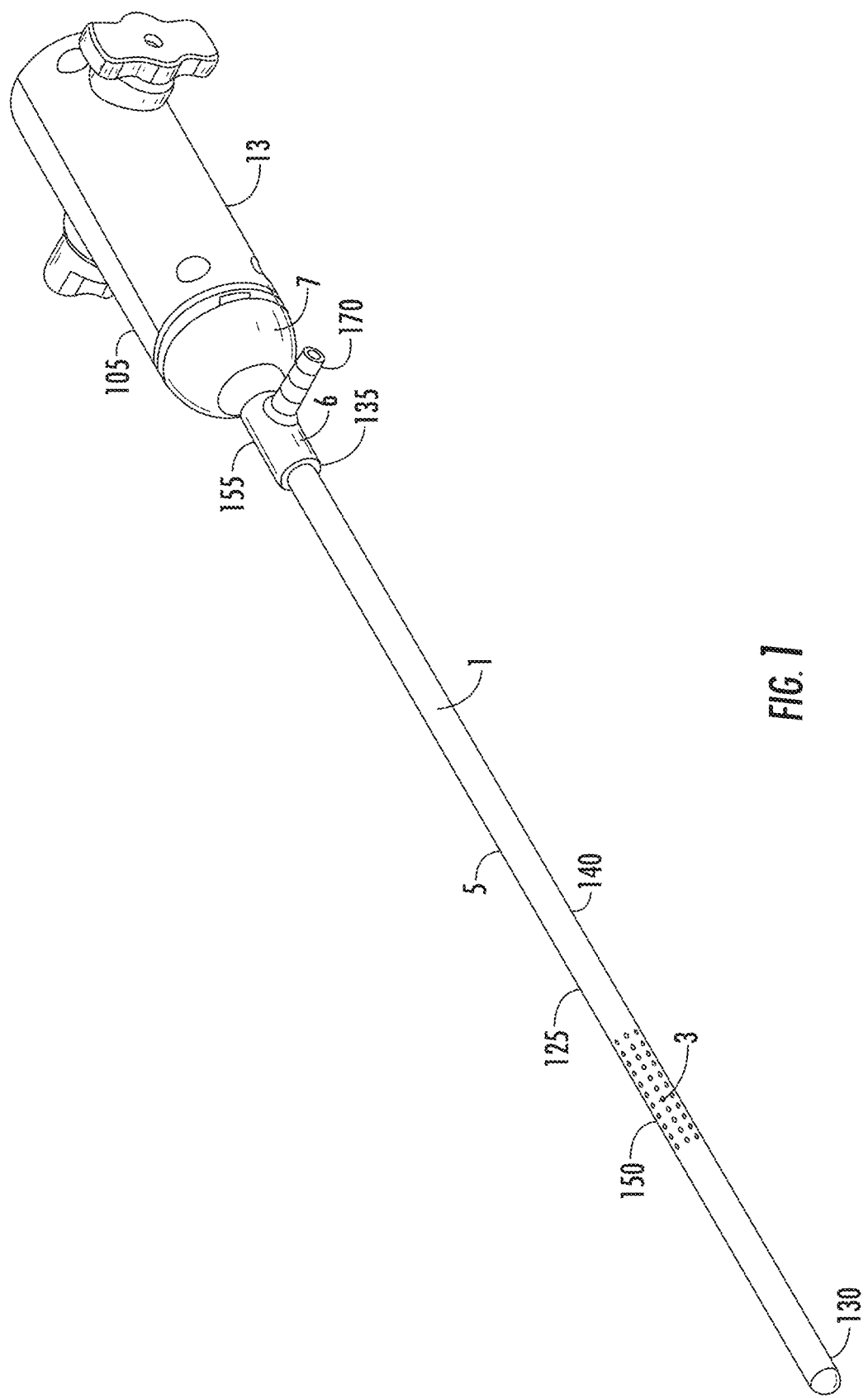
FIG. 1 is a perspective view of an example mechanical esophageal displacement system in accordance with the present disclosure.

The following is a description of several illustrations of the subject matter of Applicant's invention. Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

Figure 5:
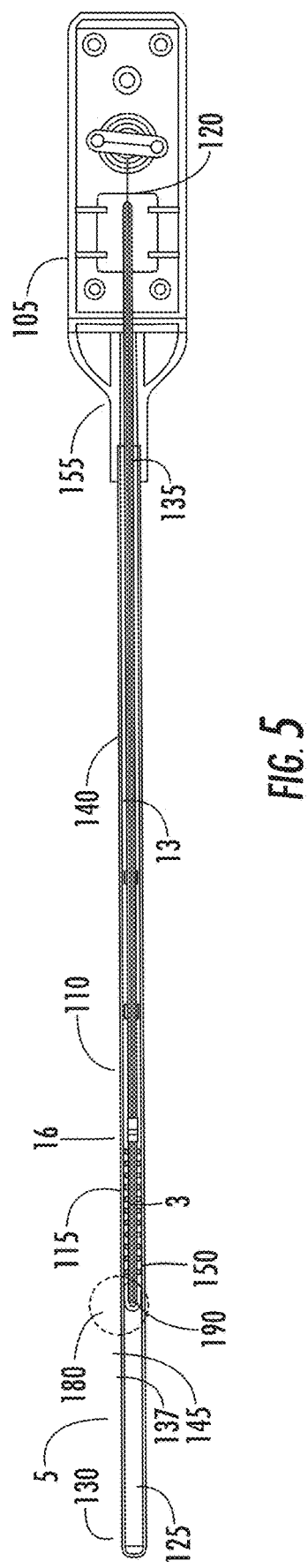
FIG. 5 is cross sectional view of the mechanical esophageal displacement system of FIG. 1.
Figure 6:
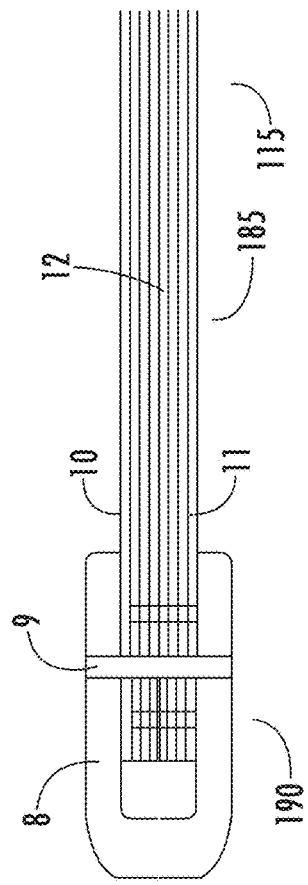
FIG. 6 is zoomed in view of a portion of the mechanical esophageal displacement system of FIG. 1.

FIGS. 1-25 show an example of a mechanical esophageal displacement system 1 in accordance with the present disclosure for mechanically displacing an esophagus during a medical procedure via vacuum suction adherence of a segment of the esophagus. As shown in FIGS. 1 and 5, the example mechanical esophageal displacement system 1 includes an assembly 5 and an esophageal positioning device 13, in which the assembly 5 is operatively coupleable to a vacuum system (not shown). In some embodiments, the assembly 5 is a disposable component of the mechanical esophageal displacement system 1, in which the assembly 5 includes one or more disposable pieces that can be removed and or replaced after a medical procedure. As will be discussed in further detail below, in some embodiments the esophageal positioning device 13 includes a handle 105, a first segment 110, a second segment 115, an articulation pivot pin 16, and an articulation driving mechanism 120. The first segment 110 and the second segment 115 may be linear structures for example.

FIGS. 2-5, 13, 25 show an example of an assembly 5 that is disposable in accordance with the present disclosure. The example assembly 5 includes an introducer 2 that is sized to receive the esophageal positioning device 13. The esophageal positioning device 13 may be a reusable component of the system 1, which is to be inserted into the lumen of the introducer 2 after the introducer is advanced down the esophagus of a patient 37. In some embodiments, however, the introducer 2 and the esophageal positioning device 13 are manufactured as a single device, and the single piece assembly 5 may be disposable or designed to be sterilized for repeated uses. The patient 37 may be a human or other animal.

Figure 2:
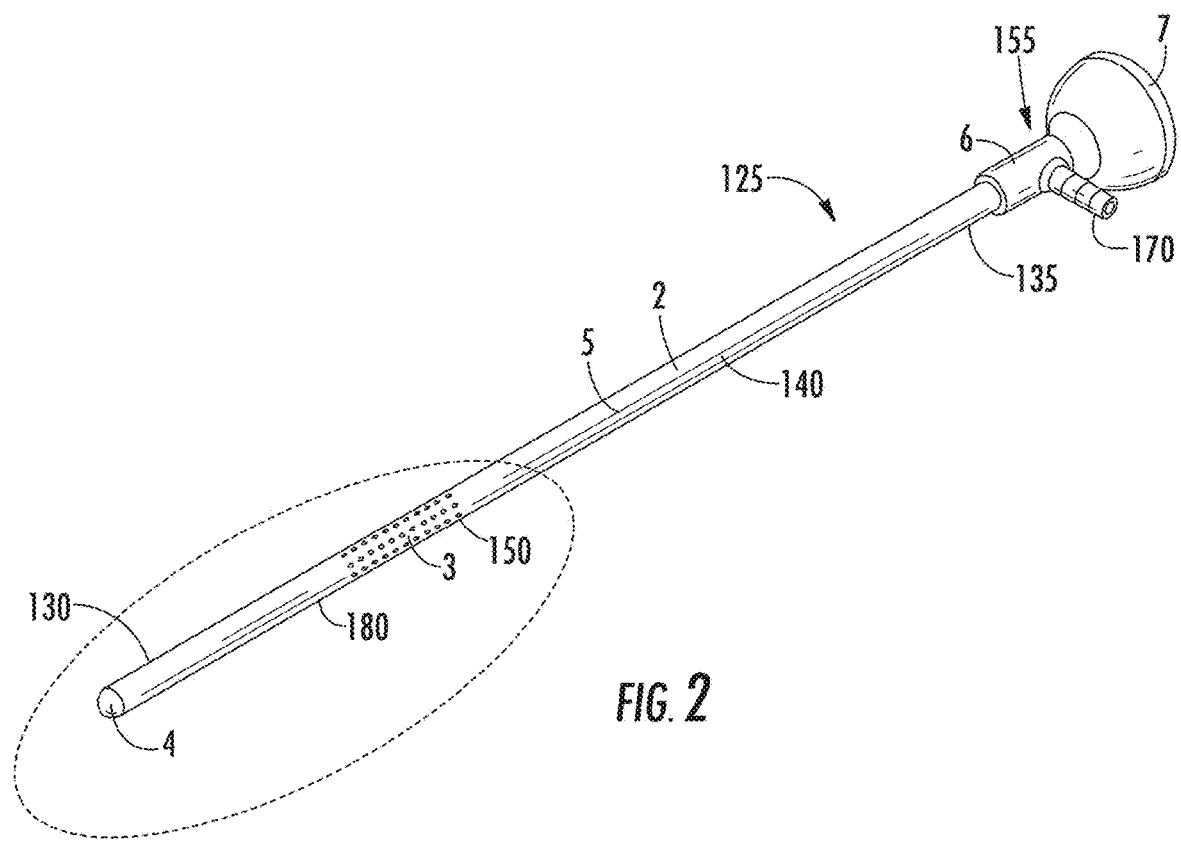
FIG. 2 is a perspective view of an example assembly of the mechanical esophageal displacement system of FIG. 1 in accordance with the present disclosure.
Figure 3:
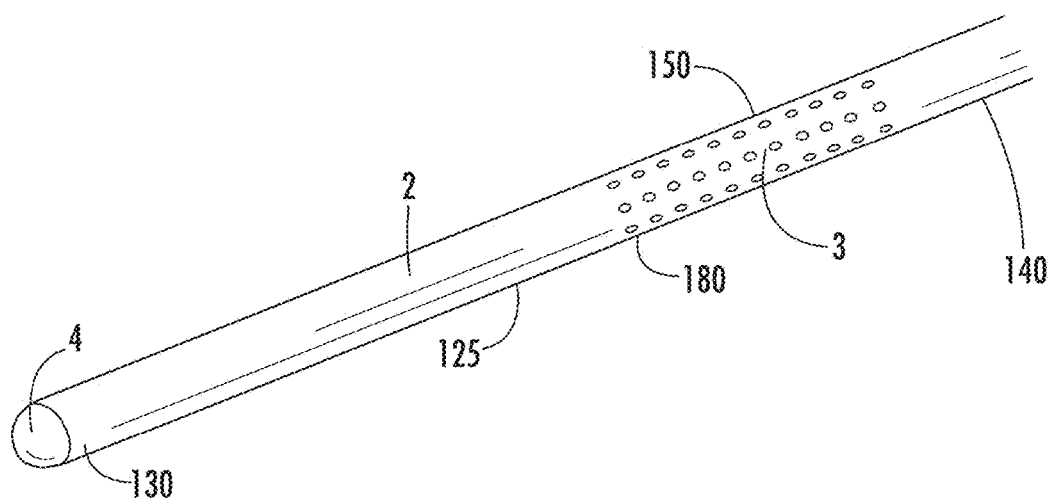
FIG. 3 is a perspective, zoomed in view, of a portion of the assembly of FIG. 2.
Figure 4:
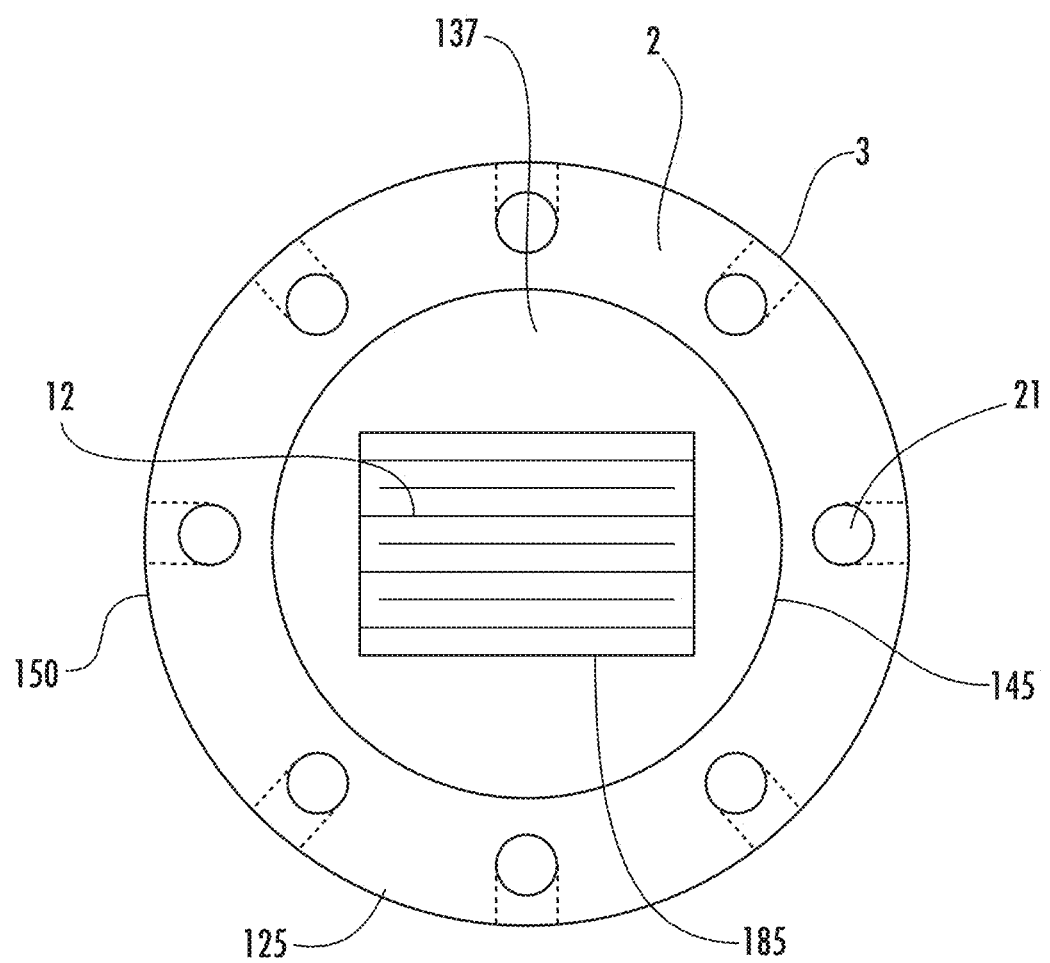
FIG. 4 is a cross sectional view of the assembly of FIG. 1.

As shown in FIG. 5, the introducer 2 includes a soft outer tube 125. In some embodiments the soft outer tube 125 is cylindrical. The soft outer tube 125 is sized such that it may pass through a mouth or nasal passage into an esophagus. The soft outer tube 125 includes a distal end 130, a proximal end 135, a lumen 137, and a body 140. In some embodiments the body 140 includes a contiguous inner surface 145. The body 140 of the outer tube includes a perforated outer surface 150 and along the length of the outer tube, and one or more internal vacuum passages 21 (see FIGS. 4 and 25) that extend a distance from the proximal end 135 towards the distal end 130 within the body 140 of the outer tube 125. In some embodiments, the perforated outer surface 150 includes a plurality of vacuum holes 3 spaced circumferentially around, and extending radially from, the soft outer tube 125, as seen in FIGS. 1-3. Because the plurality of vacuum holes 3 are spaced circumferentially around the soft outer tube 125, the plurality of vacuum holes 3 are located on multiple sides of the tube 125 and can suction the esophagus from multiple directions. The one or more internal vacuum passages 21 are in fluid communication with the plurality of vacuum holes 3 to apply a vacuum to an esophageal wall via the vacuum system. The outer tube 125, or portions thereof, can be made of, for example, a soft polymer like polyvinyl chloride (PVC) or silicone. The outer tube 125 is flexible enough to not add unnecessary stiffness to the system 1 to which the esophageal positioning device 13 would need to overcome, but not too flexible such that the outer tube 125 bunches up while inserting the introducer 2 into the esophagus. In some embodiments, the outer tube 125 includes a lubricious material coating (e.g., hydro-glide) to facilitate introduction into the esophagus and to minimize esophageal trauma.

While the outer tube 125 can be made of a single material, in some embodiments, a multi-durometer outer tube 125 is made of more than one material to achieve a desired stiffness at different portions along the outer tube 125. In some embodiments, the distal end 130 is made of a stiffer material, for example, a combination of silicone and polyurethane or other materials, while a portion between the distal end 130 and the proximal end 135 that includes a plurality of radial vacuum holes 3 is made of a more pliable material. The stiffer distal end 130 better facilitates introduction of the soft outer tube 125 into the esophagus. The more pliable material of the portion containing the plurality of radial vacuum holes 3 allow this portion of the soft outer tube 125 to collapse, creating a smaller diameter of the soft outer tube 125 and enhancing the collapse of the esophagus. Consequently, this moves the esophagus further away from the heart and provides better circumferential adherence of the esophagus to the soft outer tube 125.

In some embodiments, the assembly 5 could include a telescoping mechanism on at least a portion of the device to facilitate entry of the device into the esophagus. Once in the desired location within the esophagus, the telescoping portion could extend to deploy the entire device.

As noted above, a segment of the esophagus may be adhered to the introducer 2 via vacuum suction. To that end, the perforated outer surface 150 of the introducer 2 can include a plurality of radial vacuum holes 3 which may be positioned at various locations about the outer surface 150. In some embodiments, the plurality or radial vacuum holes 3 are positioned along the outer surface 150 starting at about between three to five inches from a tube tip 4 and span a length of about two inches from the starting location. The plurality of holes 3 are designed to be in fluid communication with the one or more internal vacuum passages 21 such that a vacuum system can create a vacuum between an esophageal wall and the outer tube 125 when the vacuum is coupled to the assembly 5 and turned on. Fluid communication may be direct or indirect. In some embodiments, the one or more internal vacuum passages 21 extend towards but not to the distal end 130. For example, in some embodiments the one or more internal vacuum passages 21 extend up to but not past the location of the most distal of the radial vacuum holes 3. In some embodiments, the one or more internal vacuum passages 21 extend through the entire length of the body 140. In some embodiments, the one or more internal vacuum passage 21 comprises one or more cylindrical rings that each or together define a cavity that are axially aligned with the lumen 137 (not shown). In some embodiments, the body 140 does not include one or more internal vacuum passages 21, but rather the plurality of radial vacuum holes 3 are in fluid communication with the lumen 137 and the vacuum is applied to the lumen 137 to create a vacuum between the esophageal wall and the outer tube 125. Any suitable vacuum system may be used that is able to provide sufficient suction to adhere a portion of the outer tube 125 to a portion of the esophageal wall. One suitable example vacuum system is a vacuum pump that provides a suction of 300 millimeters of mercury. In some embodiments, the mechanical esophageal displacement system 1 includes a feedback mechanism, such as a manometer, to confirm that a vacuum seal has been formed along the esophagus by measuring the change in pressure in the system.

As shown in FIGS. 1-3, 5, and 13, the introducer 2 can include a tube tip 4 located at the distal end 130 of the outer tube 125. In some embodiments the tube tip 4 comprises a hard polymer tip having a soft, circular contour, in which the tip is bonded to the distal end 130 of the outer tube 125, in which the tube tip 4 is a closed structure. The tube tip 4 is shaped to not harm the esophagus as the tube tip 4 is designed to be in direct contact with the esophageal passageway. The tube tip 4 may comprise a half dome shape for example. In some embodiments, the tube tip 4 is a closed structure and not luminal.

As shown in FIGS. 1, 2, 5, 13, the assembly 5 can further includes a vacuum port 155 comprising a vacuum port body 6 and a vacuum port cap 7. In some embodiments, the vacuum port cap 7 is a hard polymer cap that is bonded to the vacuum port body 6. The vacuum port cap 7 can further include a snap feature geometry and a quick release hinge mechanism (not shown) in order to couple and de-couple the handle of the esophageal positioning device 13 to the proximal end 135 of the outer tube 125. In some embodiments, the vacuum port body 6 includes a vacuum line hook up 170 that is in fluid communication with the one or more internal vacuum passages 21. The vacuum port body 6 may be bonded to both the introducer 2 and the vacuum port cap 7 to create an air tight seal. In some embodiments, the body 6 further includes a vacuum port valve and a lever (not shown), in which the lever may control the vacuum system.

In some embodiments, the introducer 2 further includes a plurality of radiopaque markers (not shown) located proximal to a location 180 where the pivot pin 16 would reside within the introducer 2. In some embodiments, the plurality of radiopaque markers span distally along or within the outer tube 125 of the introducer 2 from the location 180 of about where the pivot pin 16 would reside to the location of the tube tip 4. In some embodiments the plurality of radiopaque markers span a distance of about four to six centimeters from the tube tip 4. In some embodiments the radiopaque markers are throughout the outer tube 125.

Figure 8:
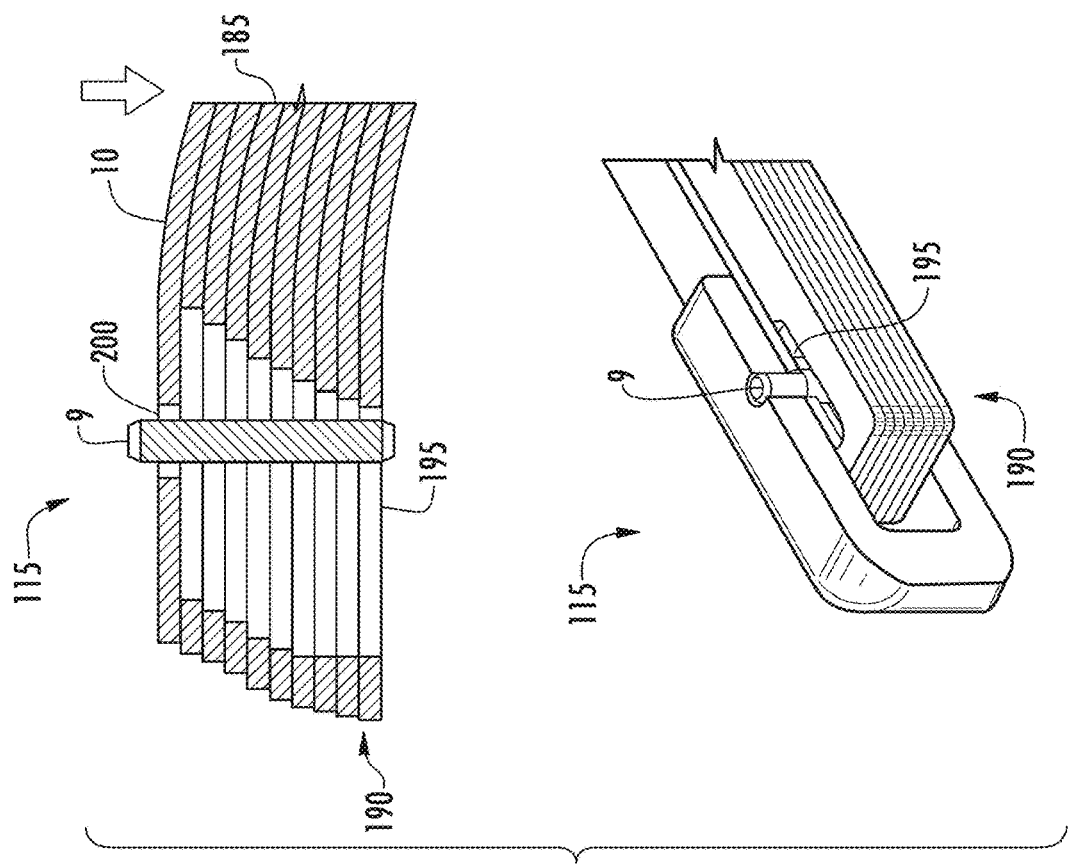
FIG. 8 is a perspective view a portion of the mechanical esophageal displacement system of FIG. 1.
Figure 7:
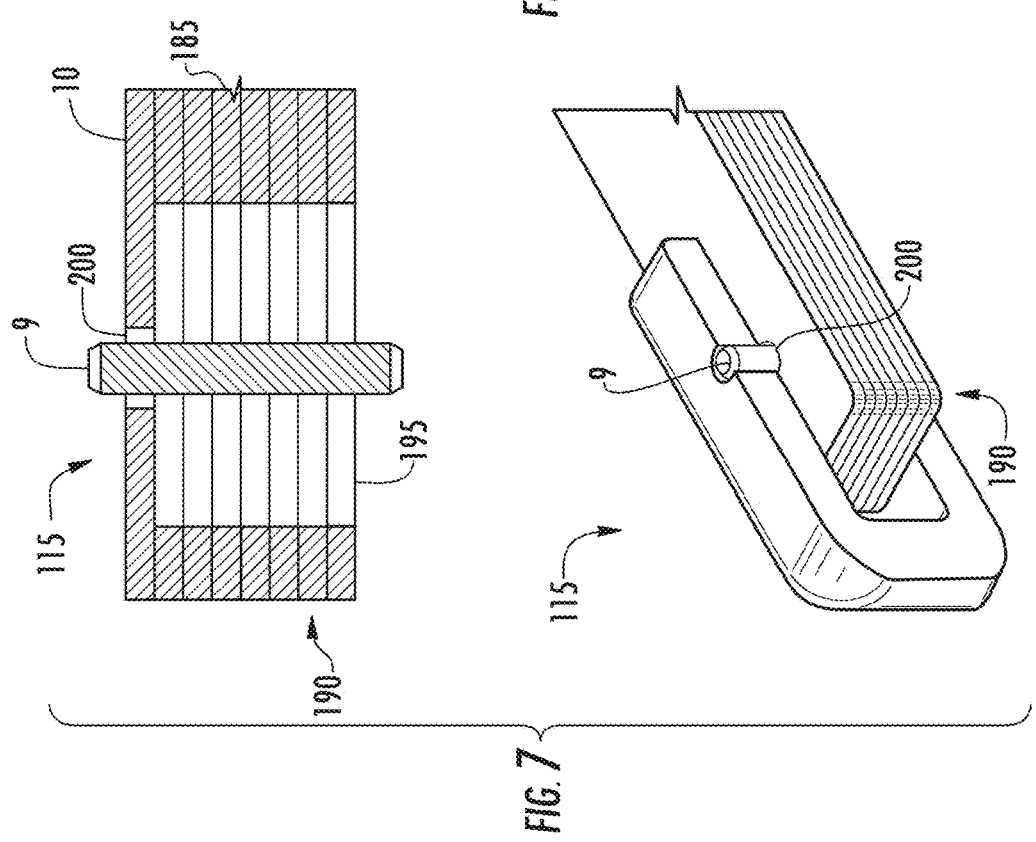
FIG. 7 is a perspective view a portion of the mechanical esophageal displacement system of FIG. 1.

As noted above, in some embodiments the esophageal positioning device 13 includes a handle 105, a first segment 110, a second segment 115, an articulation pivot pin 16, and an articulation driving mechanism 120. In some embodiments, the second segment 115 is sized to displace the esophageal wall by about 4 centimeters upon articulation. In some embodiments the second segment 115 is between four to six centimeters long. As shown in FIGS. 4-21, the second segment 115 may comprise a distal band laminate assembly 12, a distal band guard 8, and a distal pivot retainer 14, in which the distal band assembly 12 houses a plurality of distal bands 185. As shown in FIGS. 7-8, the distal band guard 8 retains the distal band assembly 12 at a distal end 190 by a pin 9 that passes through the plurality of distal bands 185. The distal band assembly 12 may be made from various suitable materials, including for example, 420 stainless steel or a hard polymer. The plurality of distal bands 185 may be made from spring steel for example. The distal pivot retainer 14 may be made of 420 stainless steel or 17-4 stainless steel for example. The plurality of distal bands 185 may be assembled to the distal pivot retainer 14 by welding, using pins or bonding. The distal bands 185 may be rigidly attached to the distal pivot retainer 14 as the bands 185 are free to flex at the distal end 190.

As shown in FIGS. 7-8, in some embodiments, all but one of the distal bands 185 has a slot 195 at a distal end as to not interfere with the pin when the bands are being flexed. One distal band 10, either the top or outer band, includes a hole 200 rather than a slot 195, in which the hole 200 restricts the band 10 from sliding when the plurality of distal bands 185 are being flexed. The hole 200 further assists with locating the plurality of distal bands 185 of the distal band assembly 12. In some embodiments the distal guard 8 has a rounded tip 205 that is free of sharp edges to prevent damage to the outer soft tube 125 during insertion.

As shown in FIGS. 10-24, in some embodiments, the first segment 110 includes a proximal pivot retainer 15, an articulation drive cable 18, and a proximal band laminate assembly 19. The proximal band assembly 19 includes a plurality of proximal bands 210. The proximal pivot retainer 15 houses the proximal laminate band assembly 19. The proximal bands 210 can be rigidly attached to the proximal pivot retainer 15 as the proximal bands 210 are free to flex at a proximal end 215 in the handle 105. In some embodiments, the proximal pivot retainer 15 limits the distal pivot retainer 14 from articulating more than a selected angle to each side, for example 45 degrees, to prevent risk of damage to the esophagus due to excessive translation.

Figure 14:
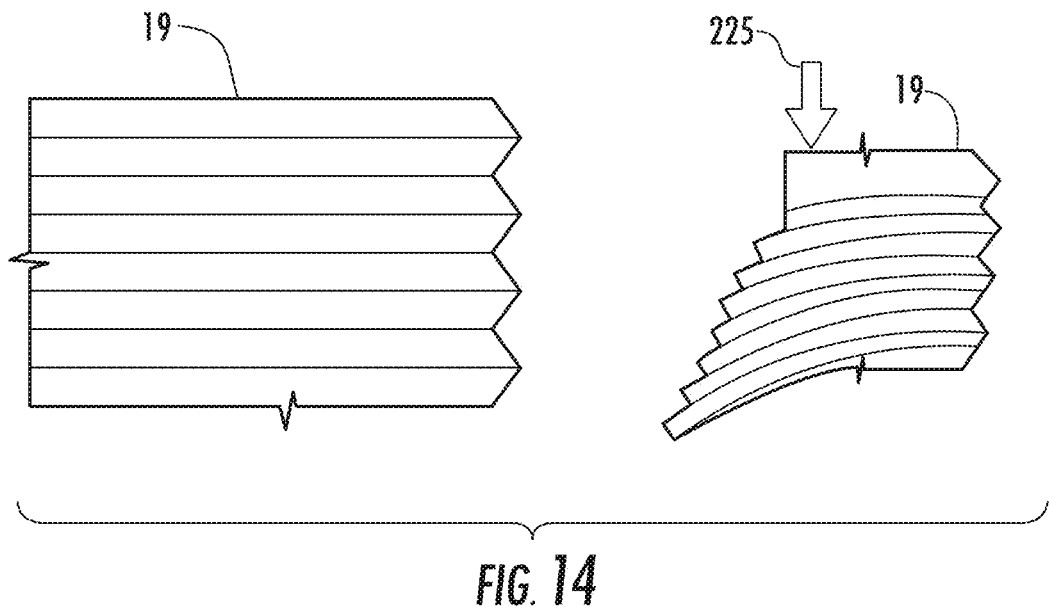
FIG. 14 is an illustrative diagram of a proximal band laminate assembly of the mechanical esophageal displacement system of FIG. 1 in accordance with the present disclosure, in which the view shows force being applied to the proximal band laminate assembly in the direction of the esophageal pathway.
Figure 15:
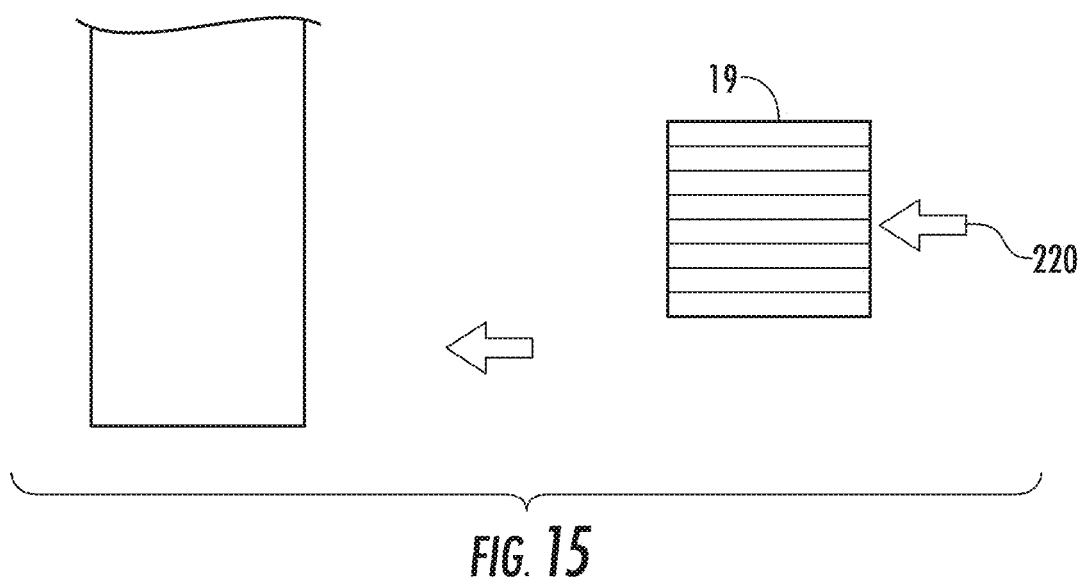
FIG. 15 is another illustrative diagram of a proximal band laminate assembly of the mechanical esophageal displacement system of FIG. 1 in accordance with the present disclosure, in which the view shows force being applied in a direction normal to the direction of the esophageal pathway.
Figure 18:
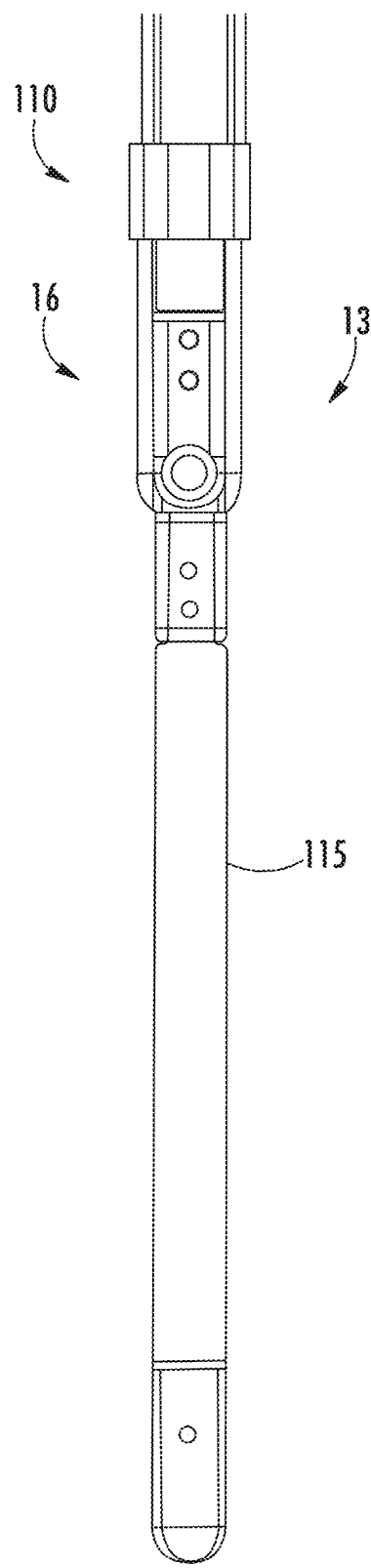
FIG. 18 shows a top view of a portion the mechanical esophageal displacement system of FIG. 1, in which the view shows an esophageal positioning device being positioned in a straight orientation.
Figures 19, 20:
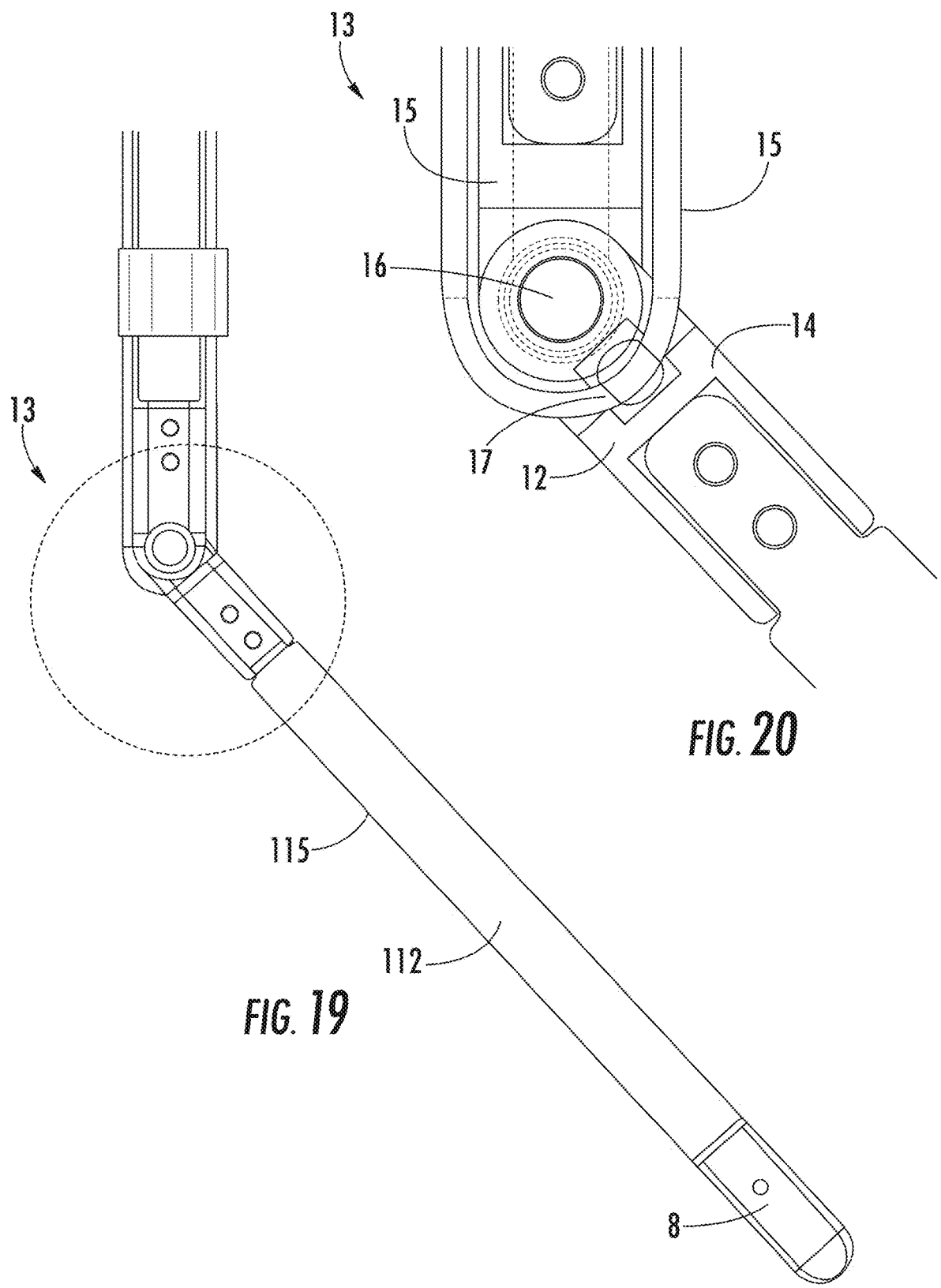
FIG. 19 shows a top view of a portion of the mechanical esophageal displacement system of FIG. 1, in which the view shows an esophageal positioning device being positioned in a second angular orientation.
FIG. 20 is a top, zoomed in, view of the portion of the esophageal positioning device of FIG. 19.
Figure 21:
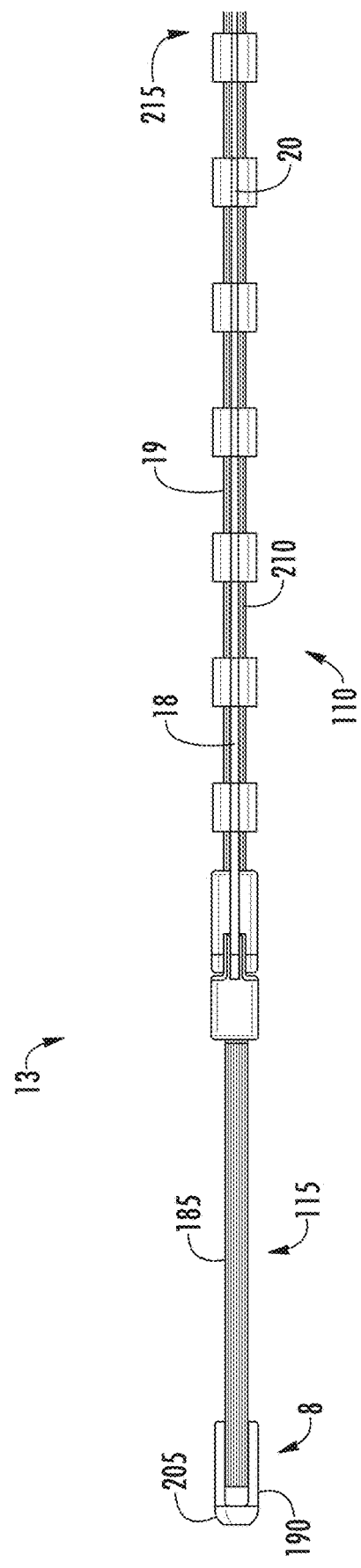
FIG. 21 is a top of a portion of the esophageal positioning device of the mechanical esophageal displacement system of FIG. 1 in accordance with the present disclosure.

As shown in FIGS. 14-15, the proximal band laminate assembly 19 may provide stiffness in a direction 220 that is normal to the direction of the esophageal pathway (FIG. 15) while maintaining flexibility in the direction 225 of the esophageal pathway. Flexibility may be maintained through the use of thin bands that are stacked on one and other (FIG. 14) to form a body that is think in the direction of the normal force provided by the esophagus (FIG. 15).

Similar to the distal band assembly 12, the proximal band laminate assembly 19 may be made from various suitable materials, including for example, 420 stainless steel or a hard polymer. The plurality of proximal bands 210 may be made from spring steel for example. The articulation pivot pin 16 may be made from 420 stainless steel or 17-4 stainless steel, for example. The articulation pivot pin 16 connects both the distal pivot retainer 14 and proximal pivot retainer 15 and allows them to pivot. The articulation pivot pin 16 may be pressure fit into the proximal pivot retainer 15 and held in a loose fit by the distal pivot retainer 14.

As shown in FIGS. 10-12, and 17-20, in some embodiments the mechanical esophageal displacement system 1 further includes an articulation drive cable 18. This cable 18 can transmit an input force by a user from the handle 105 to the articulation pivot pin 16 to articulate the second segment 110 left or right 45 degrees from the neutral position wherein the distal band assembly 12 and the proximal band assembly 19 are parallel to each other. In some embodiments, the mechanical esophageal displacement system 1 includes a feedback mechanism that measures and displays the distance the device is articulated from its neutral position. In some embodiments, the cable 18 is approximately 0.024" in diameter and is made of a braided stainless steel or polymers such as UHMWPE, Vectran or Orion. In some embodiments, the mechanical esophageal displacement system 1 further includes an articulation cable crimp 17. As shown in FIGS. 16-20, the cable crimp 17 can be a small ball, compressed and friction fit onto a stainless steel braided cable 18. This crimp 17 provides a feature on the cable 18 that can interface with the distal pivot retainer 14 when pulled to the left or right in order to articulate the system 1. The ball may be compressed and friction fit onto the articulation cable 18 to provide an interfacing surface. In some embodiments, the articulation drive cable 18 is coupled to the distal pivot retainer 14 by welding in addition to or as an alternative to a cable crimp 17. Other types of mechanical of chemical fasters may be used to operatively couple the articulation drive cable 18 to the distal pivot retainer 18, such as being integrally formed, chemically bonded, or mechanically or magnetically joined.

In some embodiments, the mechanical esophageal displacement system 1 further includes a plurality of proximal band cable guides 20 that guide the articulation cable 18 from the handle 105 to the articulation pivot pin 16, wherein the plurality of proximal band cable guides 20 are evenly spaced along the plurality of proximal bands 210. The proximal band cable guides 20 may be welded or bonded to one or more of the proximal bands 210 so as to keep the proximal bands 210 aligned while still allowing the bands 210 to slip and translate independently when bent. The proximal band cable guides 20 assist with guiding the articulation drive cables 18 down the length of the esophageal positioning device 13. The proximal band cable guides 20 provide additional stiffness and structure to the proximal band laminate assembly 19 while still allowing the laminate band assembly 19 to bend.

Figure 22:
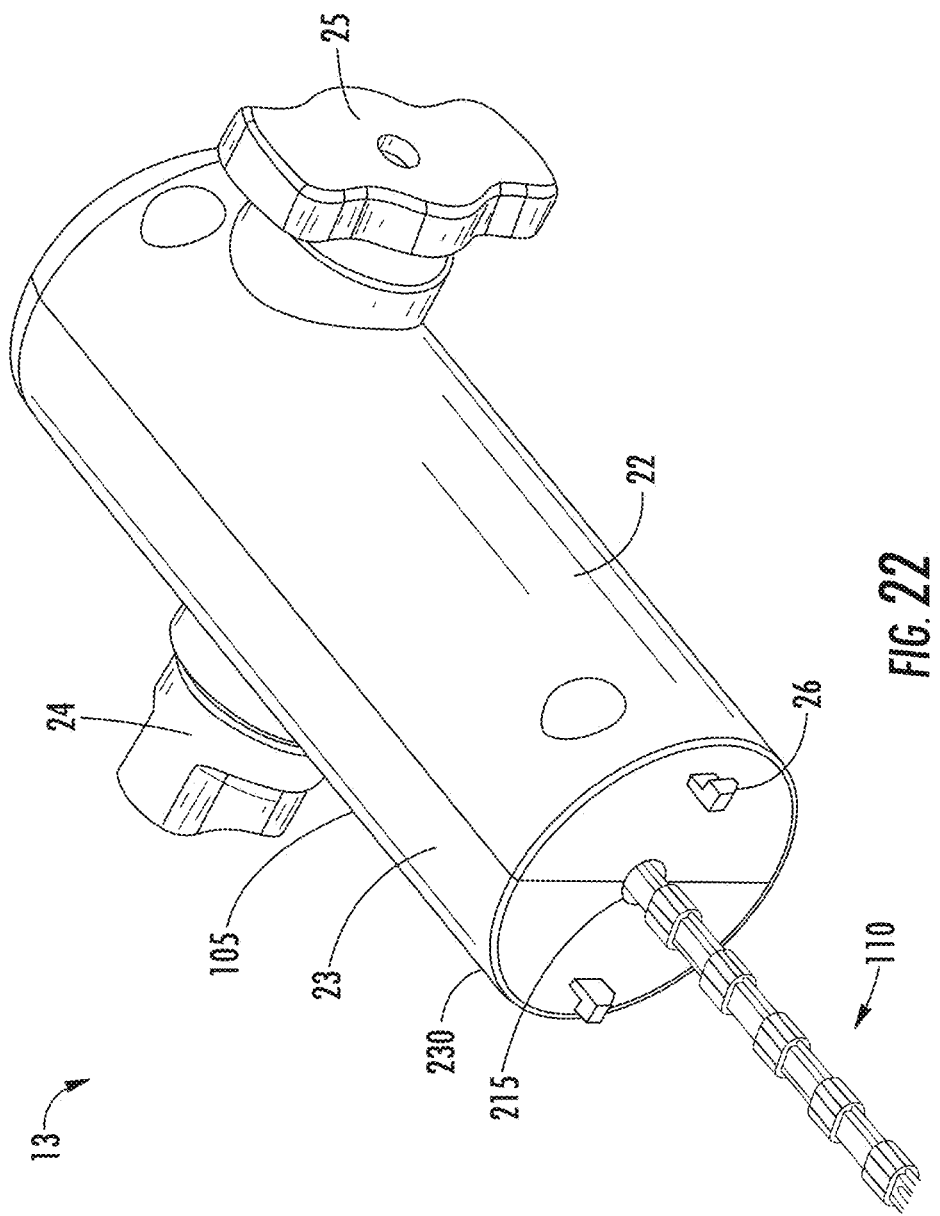
FIG. 22 is perspective view of the handle of the mechanical esophageal displacement system of FIG. 1.

As shown in FIGS. 1, 9, 13, 22-24, the handle 105 of the esophageal positioning device 13 may include a variety of components. As shown in FIG. 22, in some embodiments the handle 105 includes a two piece outer housing comprising an articulation handle case half 22 and a locking handle case half 23. In some embodiments, the articulation handle case half 22 may be made of a polymer or metal, and may be approximately 1.9" in diameter and approximately 5" long, for example. The articulation handle case half 22 may house the plurality of proximal bands 185, the articulation drive mechanism 120 as well as an articulation control knob 25. In some embodiments, the locking handle case half 23 may made of a polymer or metal, and may be approximately 1.9" in diameter and approximately 5" long, for example. The locking handle case half 23 may house the proximal bands 185, the articulation drive mechanism 120, and a locking control knob 24. The locking control knob 24 may be twisted to add friction to the system 1 as well as to completely lock the system 1 at a selected articulation angle. Twisting the locking control knob 25 in the opposite direction frees the articulation drive mechanism 120 to allow the articulation driving mechanism 120 to move freely. The knob 24 may be approximately one inch in overall diameter, for example. The articulation control knob 25 may be rotated in a first or second direction. In some embodiments, rotating the control knob in a clockwise direction may articulate the tube tip 4 of the assembly 5 to the right while rotating the control knob 25 counter clockwise may articulate the tube tip 4 of the assembly 5. The diameter of the articulation control knob 25 may be approximately two inches for example. As such, the articulating control knob 25 may articulate the second segment 115 to the right when rotated in a first direction and articulate the second segment 115 to the left when rotated in a second direction.

As shown in FIG. 22, the handle 105 of the esophageal positioning device 13 may include one or more snap hooks 26 that are located on the articulation handle case half 22 and or on the locking handle case half 23. The snap hooks 26 can be used to interface and couple the handle 105 to the vacuum port cap 7 of the assembly 5.

Figure 23:
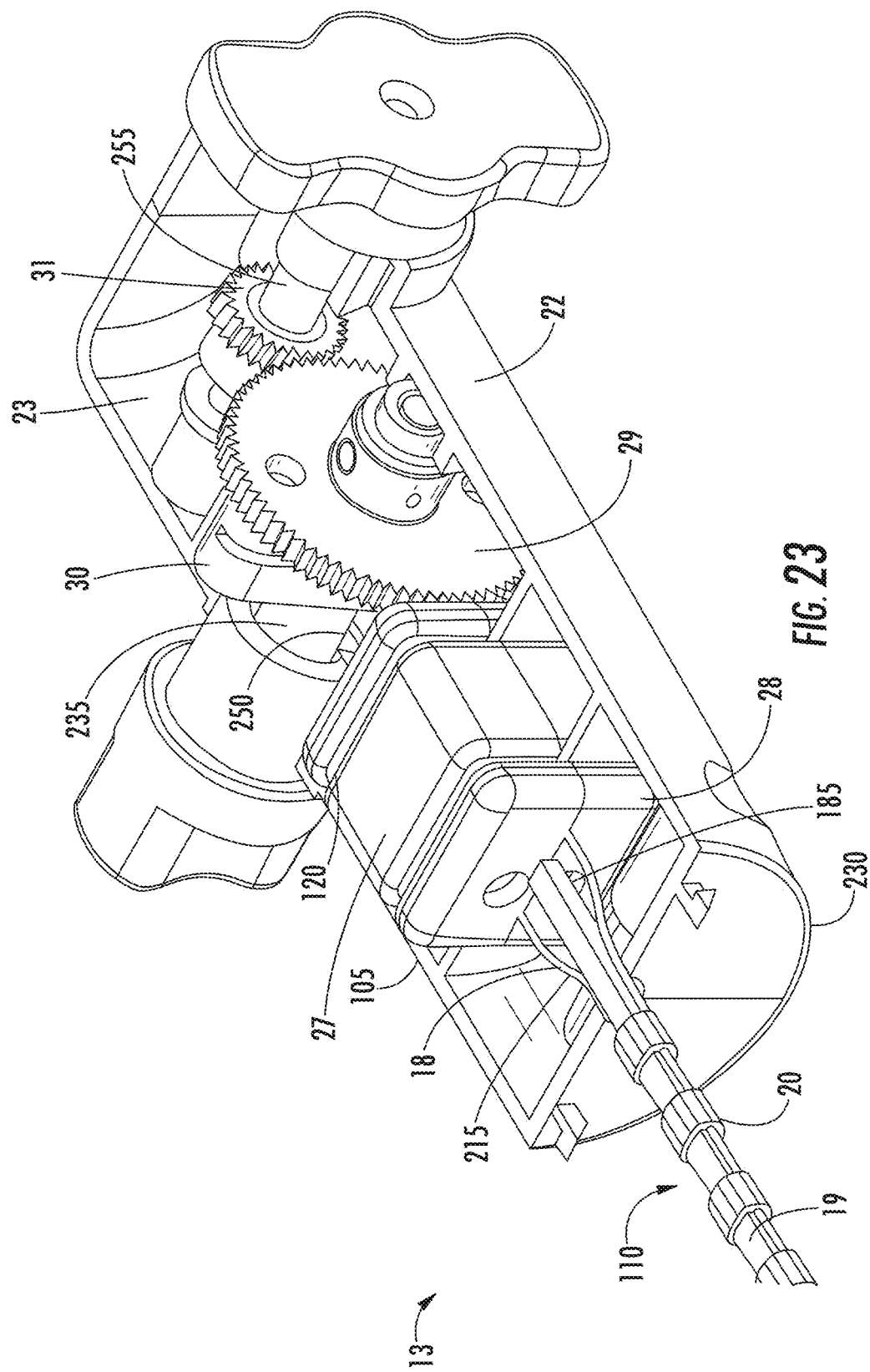
FIG. 23 is perspective view of the internal components of the handle of the mechanical esophageal displacement system of FIG. 1.
Figure 24:
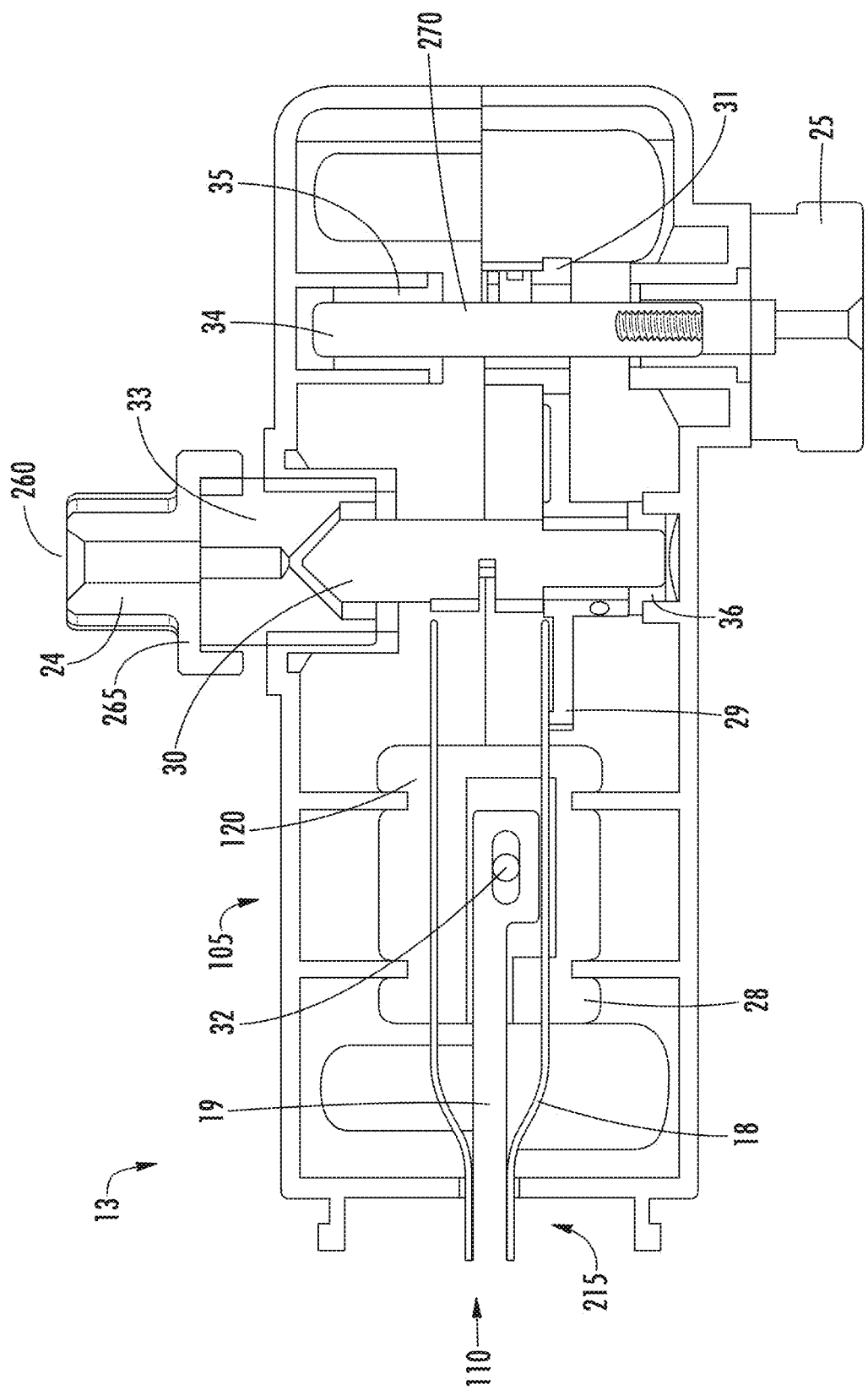
FIG. 24 is a side, cross sectional view of the internal components of the handle of FIG. 23.

As shown in FIG. 23-24, the handle 105 of the esophageal positioning device 13 may include a top handle band retainer 27, a bottom handle band retainer 28, a pulley gear 29, a cable pulley 30, an input gear 31, a proximal band handle retainer pin 32, a locking cone clutch 33, an articulation input shaft 34, an articulation input shaft bushing 35, and an articulation pulley shaft bushing 36, for example.

In some embodiments, the top and bottom handle band retainers 27, 28 house the proximal end 215 of the plurality of proximal bands 185 via pin, hole, and slot features of the proximal bands 185 to allow the bands 185 to translate while bending. The top and bottom retainers 27, 28 may be made of a polymer or aluminum, for example. The top and bottom retainers 27, 28 may be held in place together by ribs 230 found on the articulation handle case half 22 and on the locking handle case half 23.

In some embodiments, pulley gear 29 comprises a large gear that is attached to the cable pulley 30 via two pins. In some embodiments, the pulley gear 29 is concentric with the locking control knob 24 and a pulley shaft 235. In some embodiments, the pulley gear 29 is approximately two to three times larger in diameter than the diameter of the input gear 31.

In some embodiments, the articulation cables 18 are attached to the cable pulley 30 with the right side cable 18 being attached to a top pulley hole 250. The articulation cable 18 may be routed around the pins of the cable pulley 30.

In some embodiments, the input gear 31 is a small gear that is attached to an articulation control knob shaft 255 and to the pulley gear 29. The input gear 31 is used to lower the amount of input torque required by the user of the system 1 when articulating the esophageal positioning device 13. The input torque may be lowered by a factor of two to three, for example, based on a given ratio of input gear 31 to pulley gear 29. As such, in some embodiments the operator does not need to, or is restricted from, exerting more than 80 ounces per inch of torque to control the knobs 24, 25. For example, in some embodiments, a failsafe mechanism may be employed such that the articulation control knob 25 becomes locked upon an operator exerting a preset torque (e.g., more than 80 ounces per inch) to the articulation control knob 25. The lockout of the knob 25 may thus assist in avoiding injury to the operator.

In some embodiments, the proximal band handle retainer pin 32 interfaces with the proximal band laminate assembly 19, and the top and bottom handle band retainers 27, 28 to hold the proximal bands 185 in place. The proximal band handle retainer pin 32 align parts of the top and bottom handle band retainer 27, 28, when assembled together. The retain pin 32 aligns with the slots in the proximal bands 185 except for one, which allows the bands 185 to slip past one another when bending.

In some embodiments, the locking cone clutch 33 may be attached to the locking control knob 24 via a screw 260 and interfering ribs 265. The locking cone clutch 33 may include threads on an outer diameter that interface with threads of the locking handle case half 23. When the locking knob 24 is twisted, for example when twisted clockwise, the locking cone clutch 33 moves inward and interferes with a cone shaft on the cable pulley 30, which effectively slows and or locks the cable pulley 30 in its current position.

In some embodiments, the articulation input shaft 34 has a flat face that is, for example, D-shaped. The flattened face allows for interface with the input gear 31 via a set screw. The input shaft 34 may be approximately .25 inches in diameter for example. In some embodiments, the articulation input shaft bushing 35 allows the articulating input shaft 34 to freely spin. Similarly, in some embodiments, the articulation pulley shaft bushing 36 allows the articulating pulley shaft 34 to freely spin. The articulating input shaft bushing 35 and the articulating pulley shaft bushing 36 further assist in maintaining appropriate alignment of the handle 105 components.

In some embodiments, the esophageal positioning device 13 includes a clutch and or a force gauge system to limit the torque that may be exerted by a user. In some embodiments, a sensor (e.g., a thermistor or temperature sensor) is located at the distal end 190 of the esophageal positioning device 13. In some embodiments, the esophageal positioning device 13 includes multiple sensors (e.g., thermistors and/or temperature sensors) along the device to allow the measuring of temperature simultaneously at varied anatomic positions of the esophagus. In some embodiments, the thermistor, temperature, or other sensor is operatively connected to a computer, in which the computer displays a virtual image of the introducer 2 and or the esophageal positioning device 13 via a mapping screen. In some embodiments, the thermistor, temperature, or other sensor is used to display the device in a real-time imaging display (e.g., MRI, ultrasound (intracardiac, transesophageal, or transthoracic) or CT imaging), so to achieve three-dimensional imaging of the anatomy and the device. In some embodiments, the introducer 2 or the esophageal positioning device 13 includes a port to receive a gastrograffin injection or other material used to outline and visualize the esophagus on an x-ray. In some embodiments a ratcheting articulation control is provided such that one click of the ratcheting articulation control knob in a counter clockwise direction could causes 15 degrees of articulation to the left or 1.5 cm of translation to the left depending on which is desirable for the operator. In some embodiments audible clicks are provided as feedback to the operator as to the mount of tension being deliver to a knob. In some embodiments, a safety release mechanism is incorporated into the esophageal positioning device 13 so to prevent excessive force upon the esophagus.

In some embodiments, the esophageal positioning device 13 includes other imaging devices for use with visualizing techniques. Such imaging devices can include, for example, a fiber optic light source with a camera, ultrasound imaging (e.g., Doppler), etc. These imaging devices can be used to visualize the esophagus before, during, and after application of ablation energy and at other times during the procedure. The ultrasound imaging can be used, for example, to visualize and measure through the esophagus to view intracardiac objects such as catheters, transseptal techniques/equipment, evaluation of intracardiac thrombi, evaluation of intracardiac defects such as an atrial septal defect, visualize/measure pulmonary vein devices, visualize/measure mapping devices (e.g., multi-electrode baskets), visualize/measure the left atrial appendage and left atrial appendage closure devices, visualize/measure devices placed inside the pericardium, and other cardiac related products.

Figure 25:
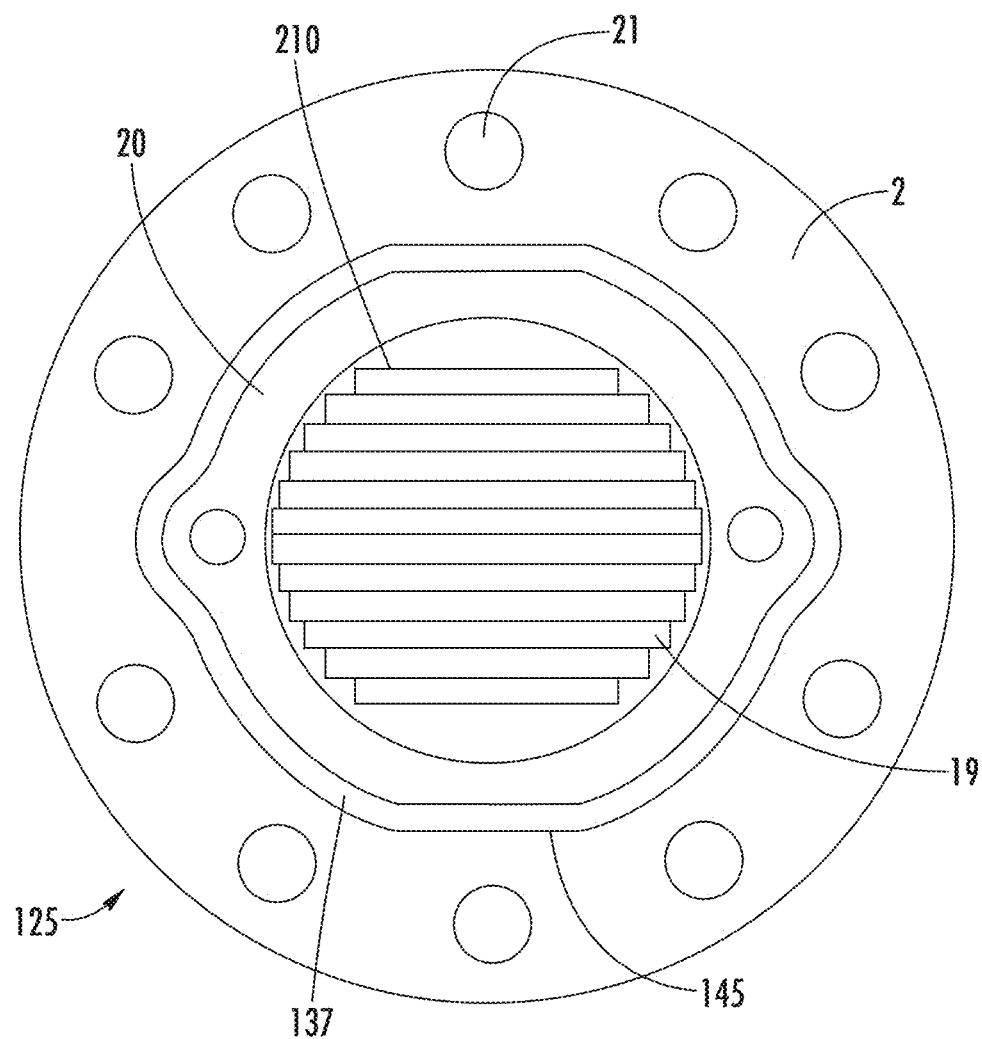
FIG. 25 is a cross sectional view of another example assembly of the mechanical esophageal displacement system of FIG. 1.

In some embodiments the band laminates of the distal or proximal band assemblies 12, 19 have differing widths. FIG. 25 shows an example of a proximal band assembly 19 having proximal bands 210 having differing widths. The widths of the distal or proximal bands 185, 210 can be shaped to maximize stiffness depending on profile shape of the outer tube 125 of the introducer 2. For example, if the profile shape the outer tube 125 of the introducer 2 is circular, the distal or proximal bands 185, 210 may be cut such that the profile of the bands 185, 210 take the shape of a circle. The use of differing widths can provide a more space efficient interaction between the bands 185, 210 and the outer tube of the introducer 2 or cable band guide 20. Moreover, cutting the bands of the proximal assembly 19 (or distal assembly 12) in different widths may increases the stiffness of the system 1 as the amount of material that is in contact with the inner surface of the outer tube or cable band guide 20 is increased.

Although many materials are disclosed for the various parts of the assembly 5, in some embodiments, all parts of the assembly 5 are made of non-ferrous materials to allow for use with advanced mapping systems or in an MRI procedure room.

Figure 13:
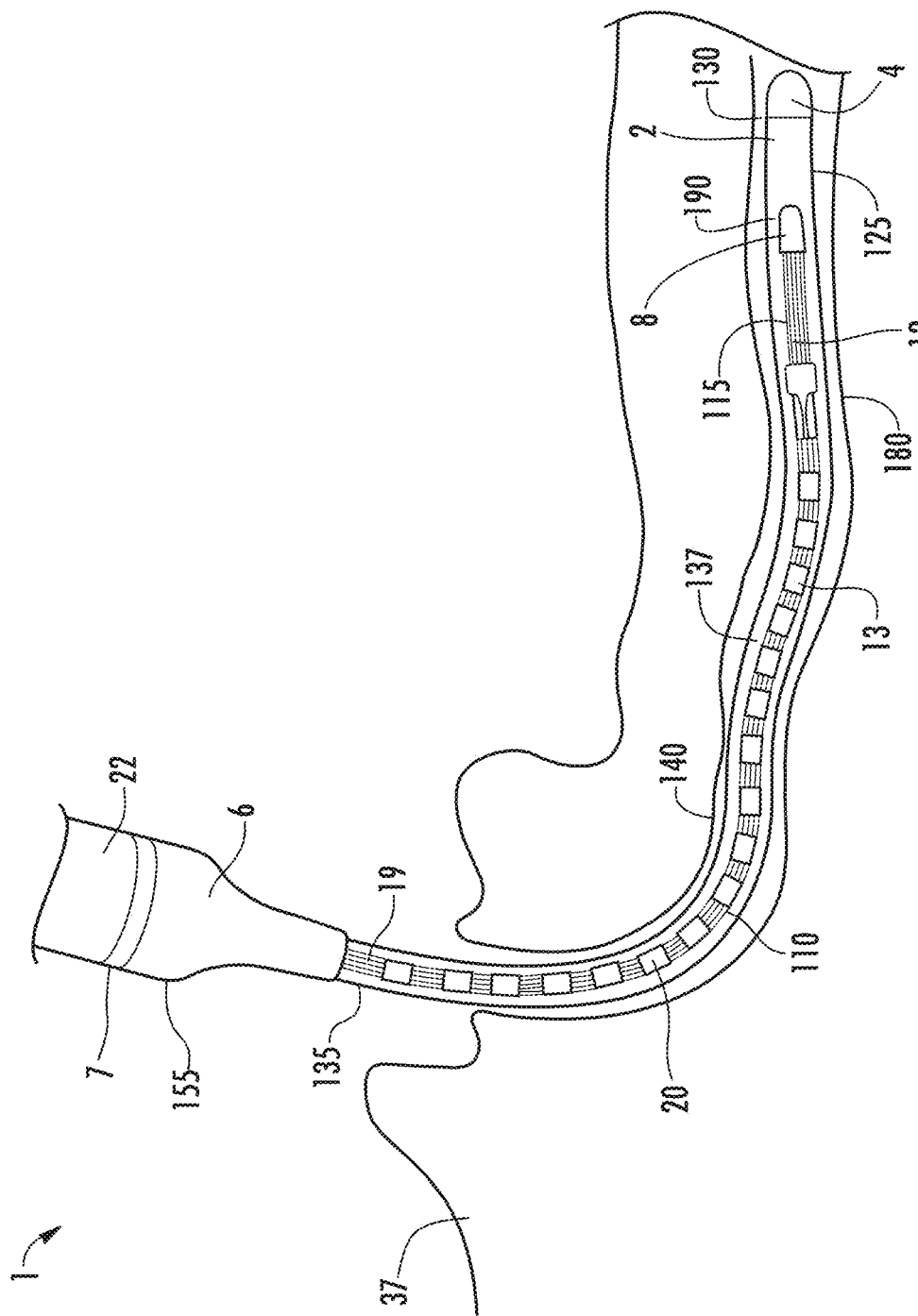
FIG. 13 is an illustrative diagram of the mechanical esophageal displacement system of FIG. 1, in which the view shows the mechanical esophageal displacement system being advanced down the esophagus of a patient.

Also provided are methods of using a mechanical esophageal displacement system 1. An example method includes inserting an assembly 5 into an esophagus of a patient 37 via a mouth or nasal passage (FIG. 13). The assembly 5 includes an introducer 2 having a soft cyclical outer tube 125, a vacuum port 155, and a tube tip 4. The soft outer tube 125 being sized to pass through a mouth or nasal passage of a patient into an esophagus, in which the soft outer tube 125 includes a distal end 130, a proximal end 135, a lumen 137 (see FIGS. 4 and 25), and a body 140. The body 140 of the outer tube 125 includes a perforated outer surface 150, and one or more internal vacuum passages 21 that extend a distance from the proximal end 135 towards the distal end 130 within the body 140 of the outer tube 125. In some embodiments, the perforated outer surface 150 includes a plurality of vacuum holes 3 spaced circumferentially around, and extending radially from, the soft outer tube 125, as seen in FIGS. 1-3. Because the plurality of vacuum holes 3 are spaced circumferentially around the soft outer tube 125, the plurality of vacuum holes 3 are located on multiple sides of the tube 125 and can suction the esophagus from multiple directions. The one or more internal vacuum passages 21 are in fluid communication with the plurality of vacuum holes 3 to apply a vacuum to an esophageal wall via the vacuum system. The tube tip 4 being located at the distal end 130 of the outer tube 125. The vacuum port 155 includes a vacuum port body 6, a vacuum line hook up 170, and a vacuum port cap 7. In some embodiments, the body includes a contiguous inner surface 145.

The example method further includes advancing an esophageal positioning device 13 through the outer tube of the introducer 2, in which the esophageal positioning device 13 includes a handle 105, a first segment 110, a second segment 115, an articulation pivot pin 16, and an articulation driving mechanism 120. The first segment 120 being coupled to the handle 105. The second segment 115 being pivotally connected to the first segment 110 via the articulation pivot pin 16. The articulation driving mechanism 120 being configured to pivot the second segment 115 about the first segment 110 upon articulation.

The example method further includes snapping the handle 105 of the esophageal positioning device 13 to the vacuum port cap 7 of the introducer 2, engaging the vacuum system to adhere a portion of the outer tube 125 to an esophageal wall, and articulating the articulation driving mechanism 120 to pivot the second segment 115 about the first segment 110 to a selected angle, for example an angle of about 45 degrees.

Figure 26:
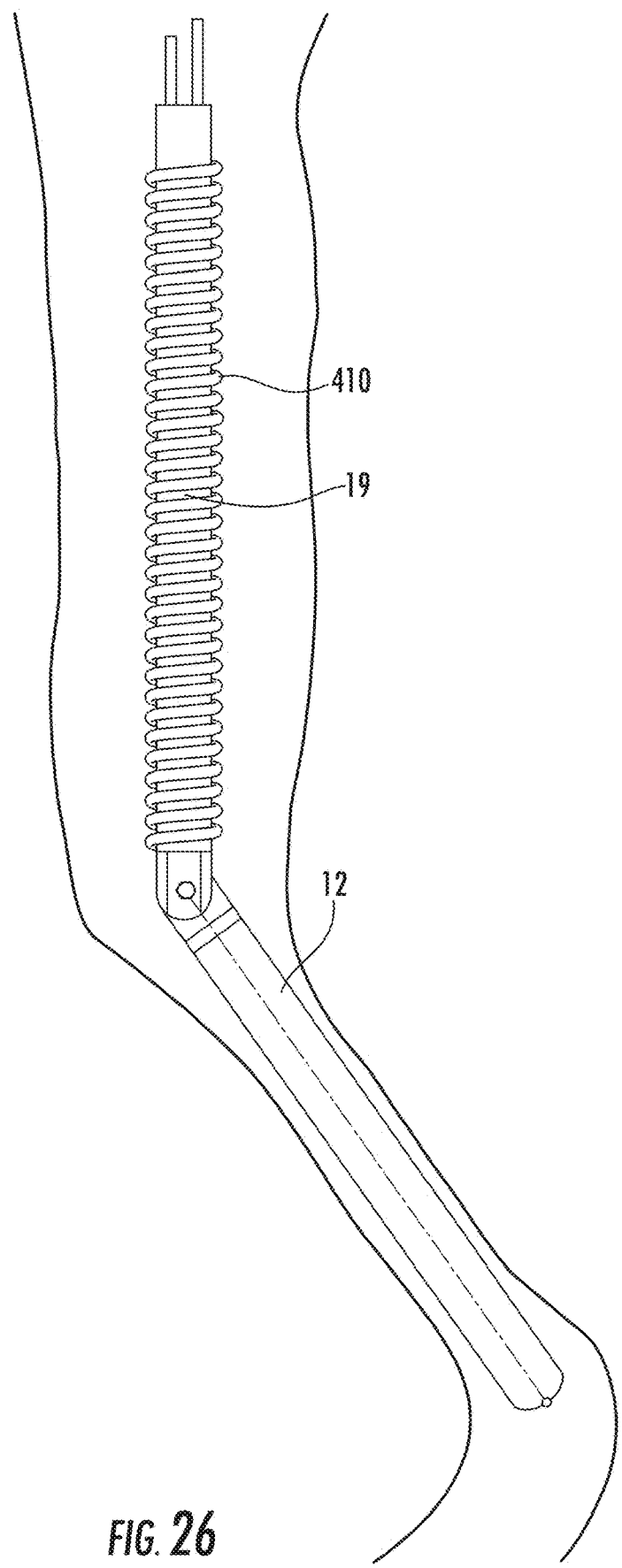
FIG. 26 is a top view of another example mechanical esophageal displacement system in accordance with the present disclosure.

FIG. 26 shows another example mechanical esophageal displacement system in accordance with the present disclosure. The mechanical esophageal displacement system includes a flexible coil 410 wrapped around a portion of the esophageal displacement device. Similar to the embodiment found in FIG. 1 above, the example mechanical esophageal displacement system of FIG. 26 can displace the esophagus about 4 centimeters, for example, 3.992 centimeters.

Figure 27:
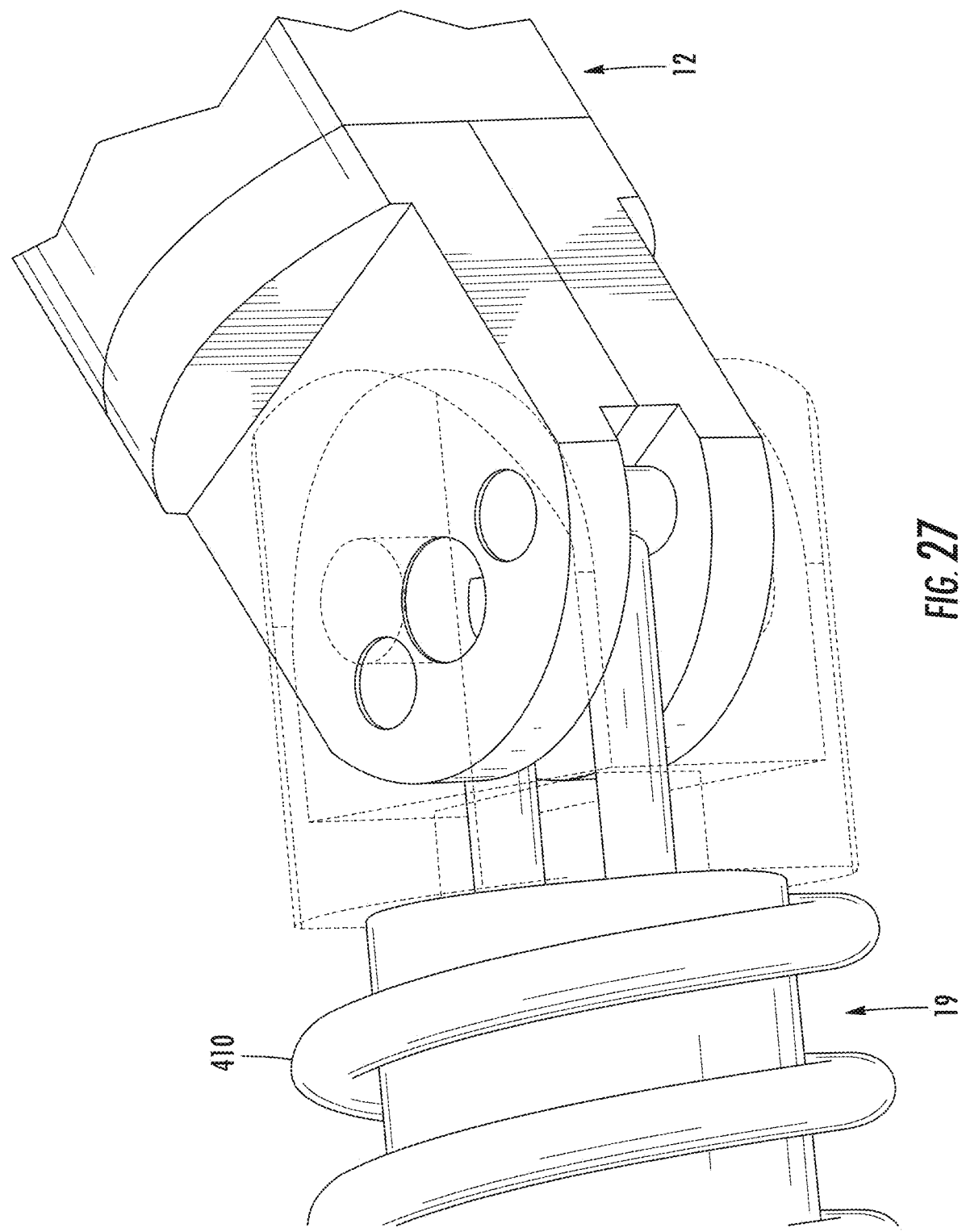
FIG. 27 is a perspective, zoomed in view of the example mechanical esophageal displacement system of FIG. 26.
Figure 28:
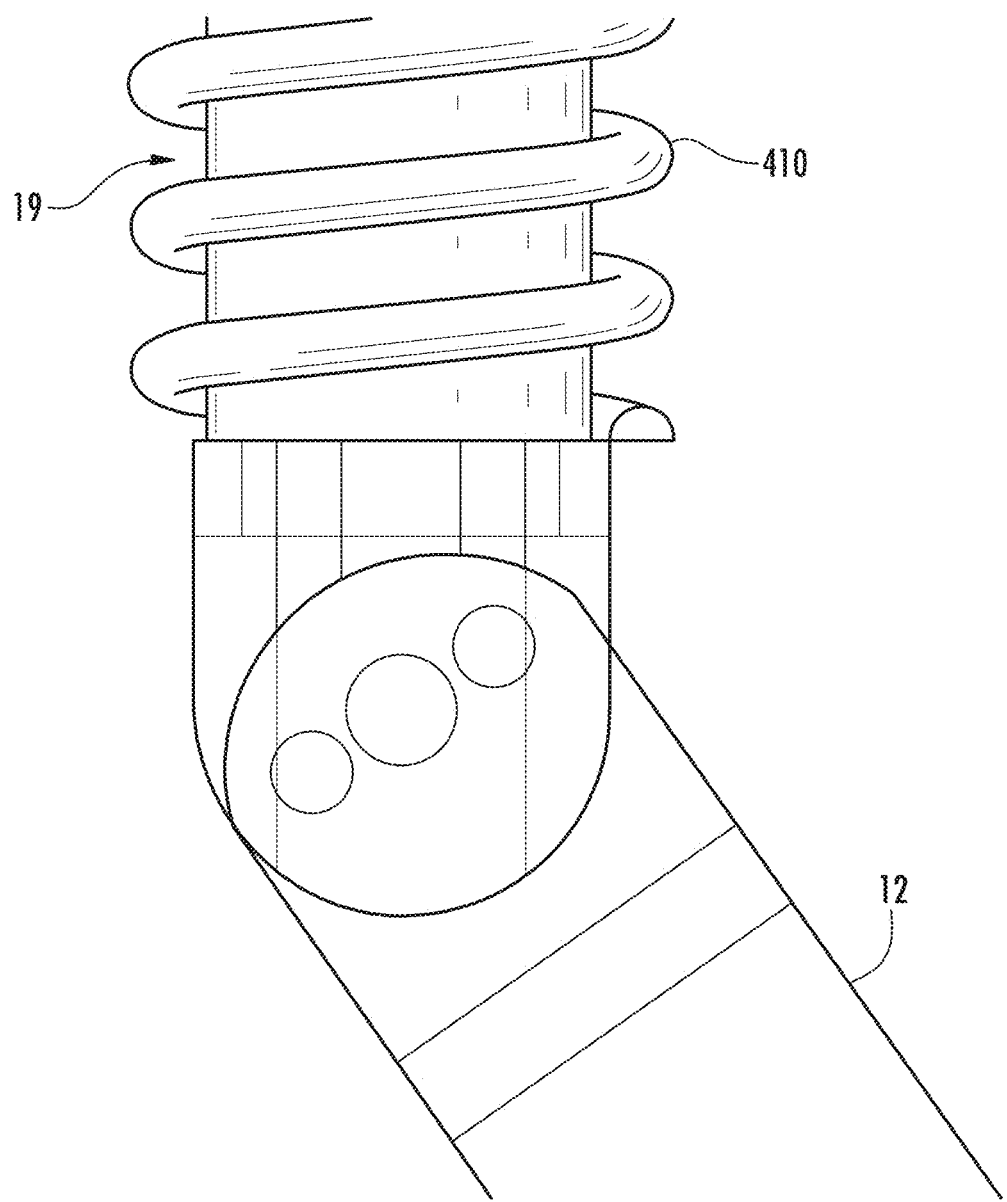
FIG. 28 is a top, zoomed in view of the example mechanical esophageal displacement system of FIG. 26

FIG. 27 is a perspective, zoomed in view of the example mechanical esophageal displacement system of FIG. 26. The view highlights an articulation pin that is operatively coupled to a coil to articulate the segments of the esophageal positioning device about the pin. FIG. 28 is a top, zoomed in view of the example mechanical esophageal displacement system of FIG. 26, in which the view highlights example dimensions.

Figure 29:
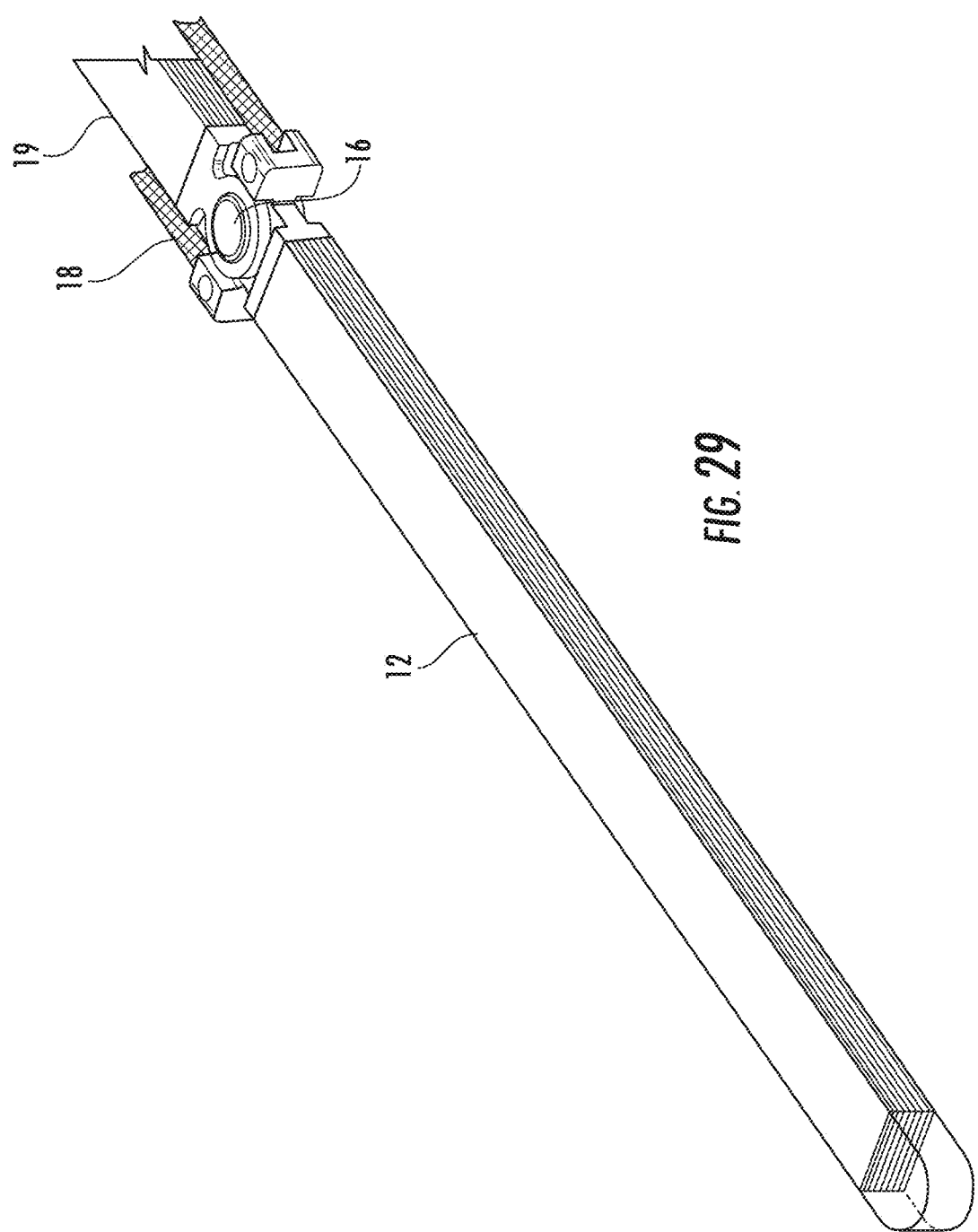
FIG. 29 is a perspective view of another example mechanical esophageal displacement system in accordance with the present disclosure.

FIG. 29 is a perspective view of another example mechanical esophageal displacement system in accordance with the present disclosure. Similar to the embodiment found in FIG. 1 above, the example mechanical esophageal displacement system of FIG. 29 includes pulleys and cables to articulate the respective segments of the esophageal positioning device.

Figure 30:
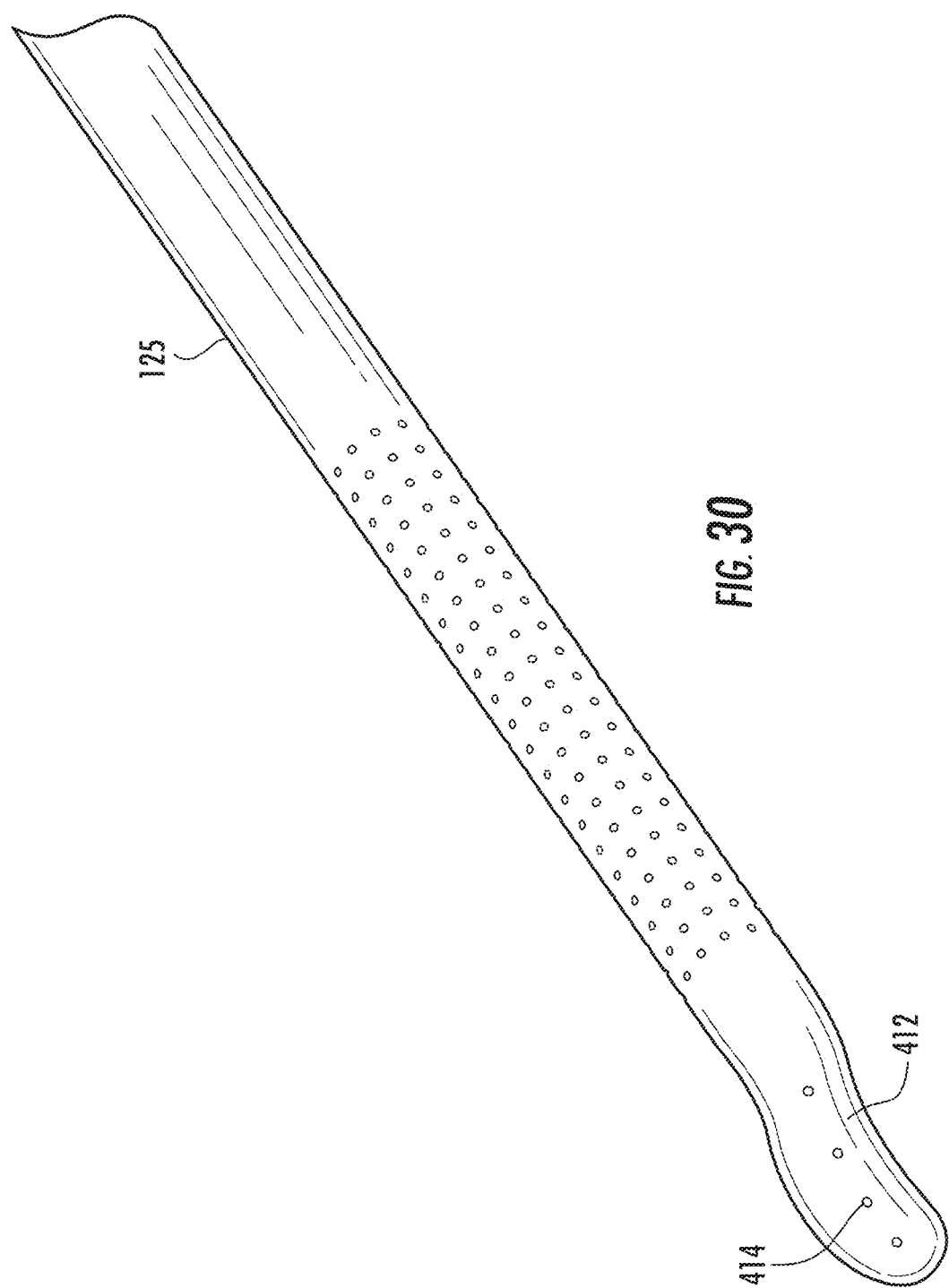
FIG. 30 is a perspective view of an example assembly of the mechanical esophageal displacement system of FIG. 29.

FIG. 30 is a perspective view of an example assembly of the mechanical esophageal displacement system of FIG. 29. The view shows an outer tube 125 having a long tail 412 with radiopaque markers 414.

Figure 31:
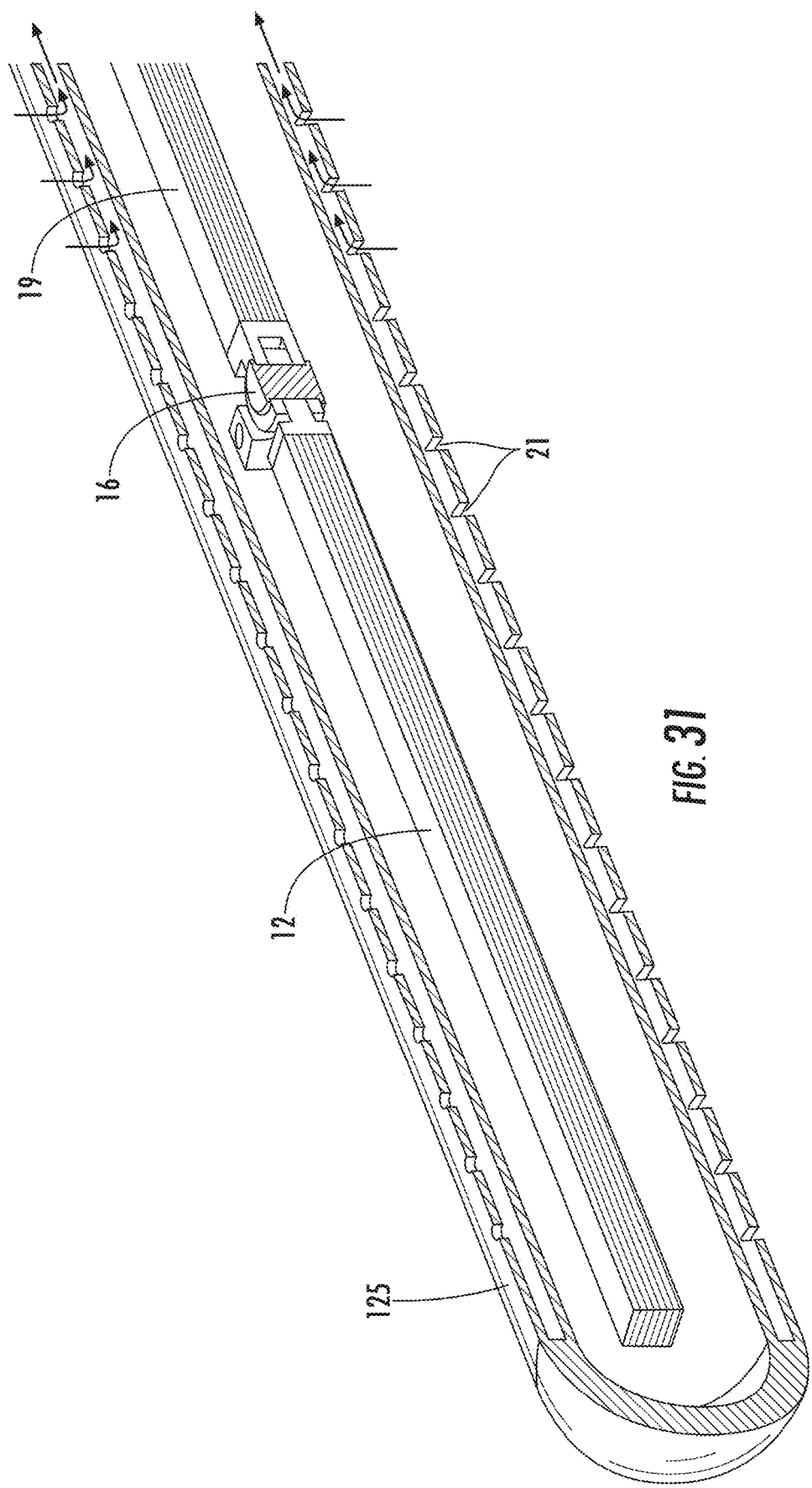
FIG. 31 is perceptive, cross sectional view of a portion of portion of the mechanical esophageal displacement system of FIG. 29.

FIG. 31 is perceptive, cross sectional view of a portion of the mechanical esophageal displacement system of FIG. 29. The view highlights vacuum passages 21 and holes of the assembly.

Figure 32:
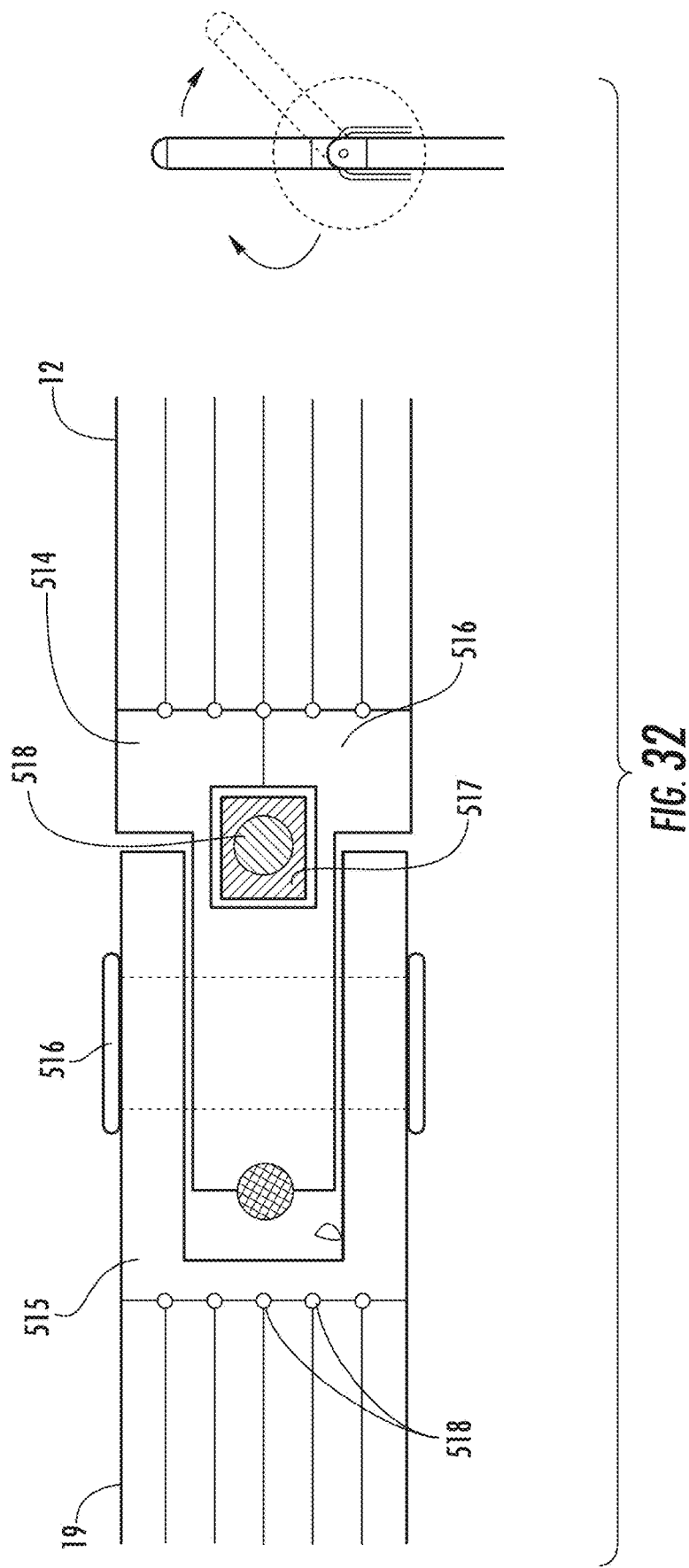
FIG. 32 is a front view of a portion of portion of the mechanical esophageal displacement system of FIG. 29.

FIG. 32 is a front view of a portion of the mechanical esophageal displacement system of FIG. 29. The view highlights the connection between the segments of the esophageal positioning device. The view includes a clevis 515, pin 516, cable 518, crimp 517, welds 518, and top 514 and bottom 516 pulley halves.

Figure 33:
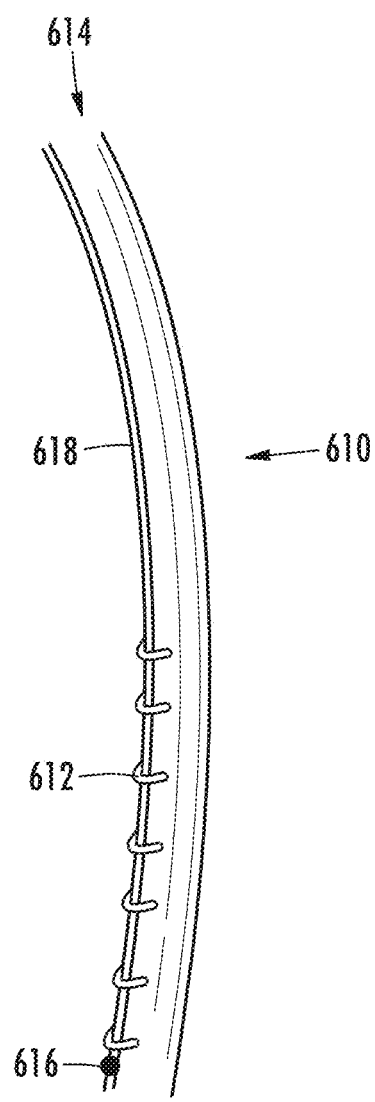
FIG. 33 is a perceptive view of another example mechanical esophageal displacement system in accordance with the present disclosure.

FIG. 33 is a perceptive view of another example mechanical esophageal displacement system in accordance with the present disclosure. The view shows an esophageal positioning device having a fishing rod 610, eyelets 612, a cinch wire 614, and cables 618, in which the cables house an anchor 616.

Figure 34:
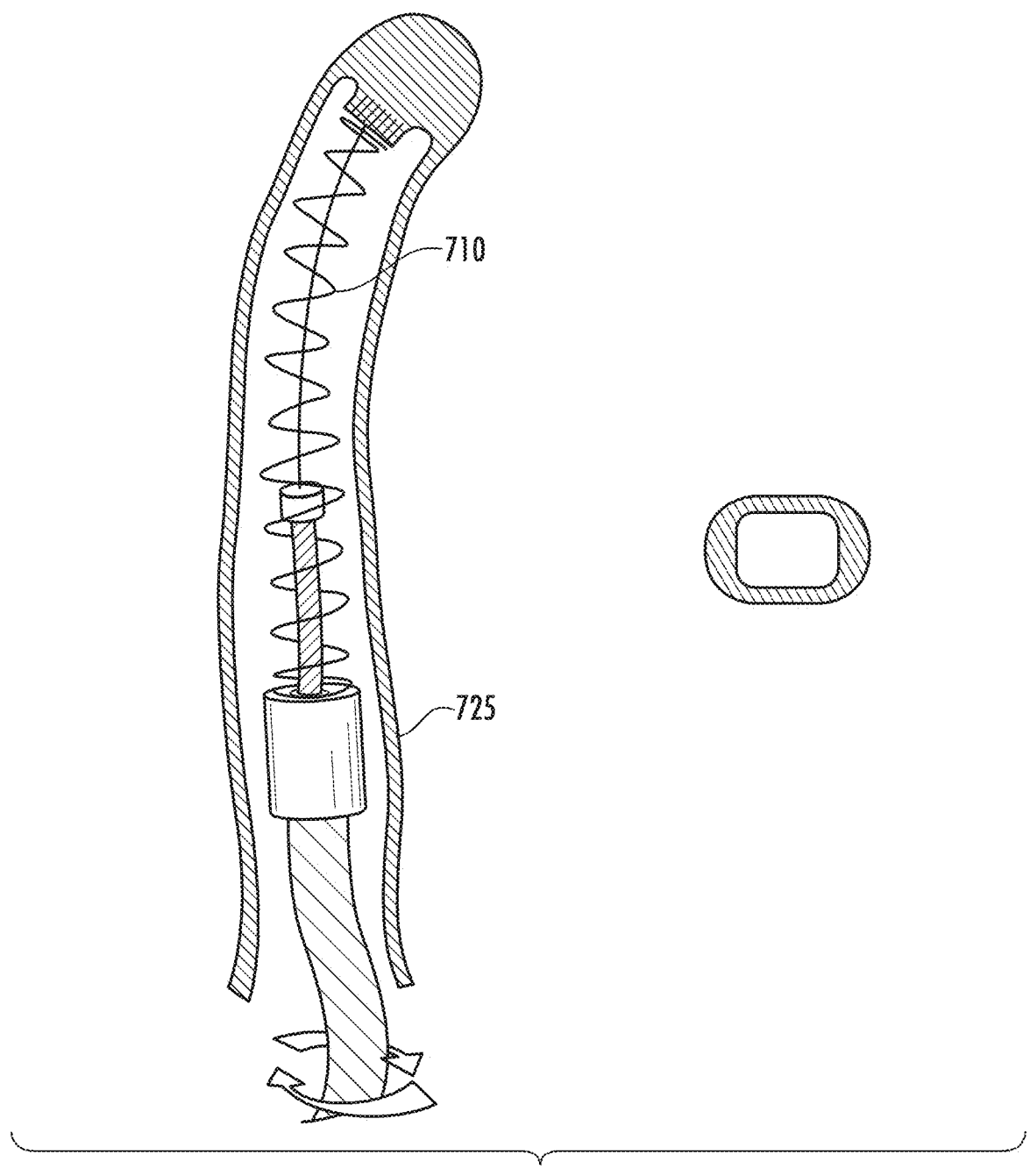
FIG. 34 is a perceptive, cross sectional view of another example mechanical esophageal displacement system in accordance with the present disclosure.

FIG. 34 is a perceptive, cross sectional view of another example mechanical esophageal displacement system in accordance with the present disclosure. The mechanical esophageal displacement system of FIG. 34 includes an esophageal displacement device that rotates to compress a spring 710 operatively coupled to the assembly.

Figure 35:
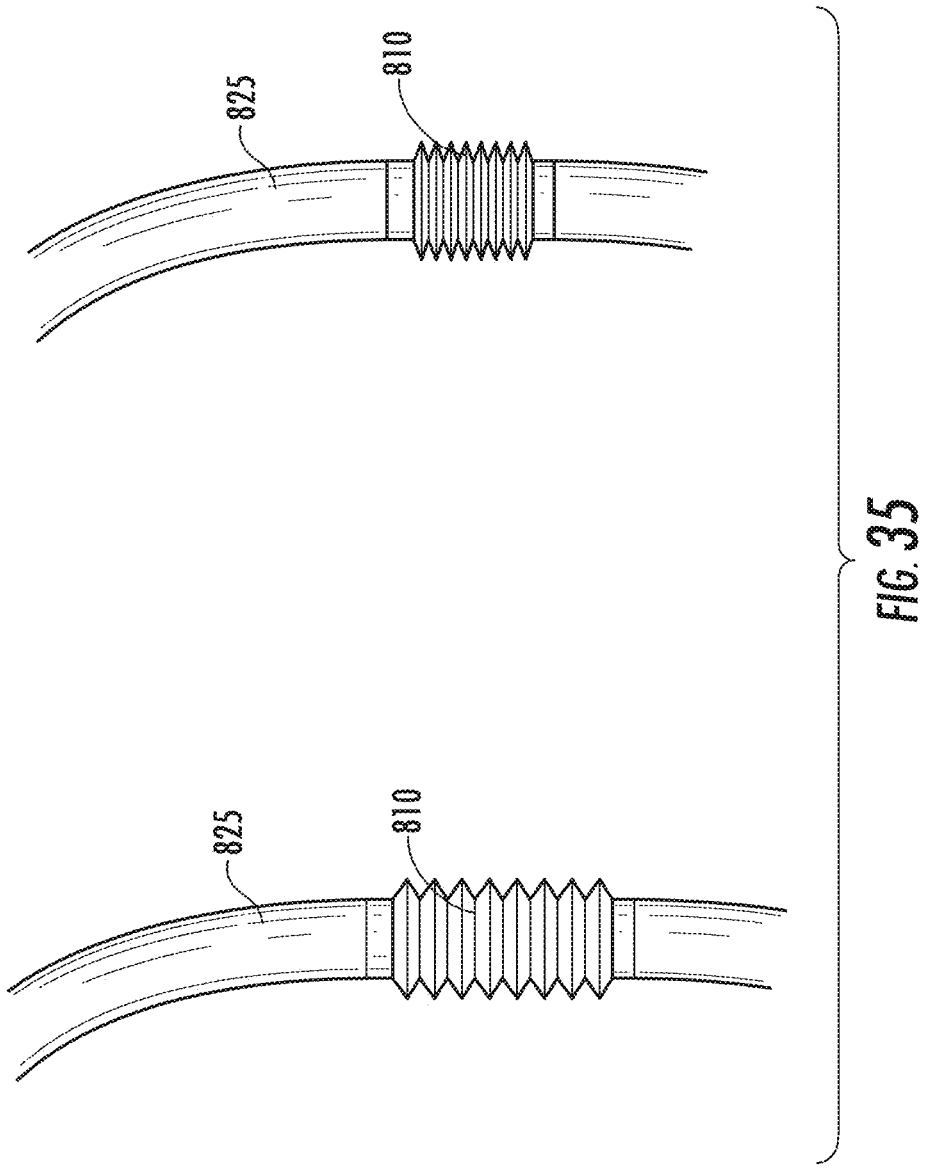
FIG. 35 is a perspective view of another example assembly in accordance with the present disclosure.

FIG. 35 is a perspective view of another example assembly in accordance with the present disclosure. In FIG. 35, the assembly includes a tube 825 having a collapsible portion 810, in which the collapsible portion 810 can be actuated by guide wires and/or vacuum pressure.

Figure 36:
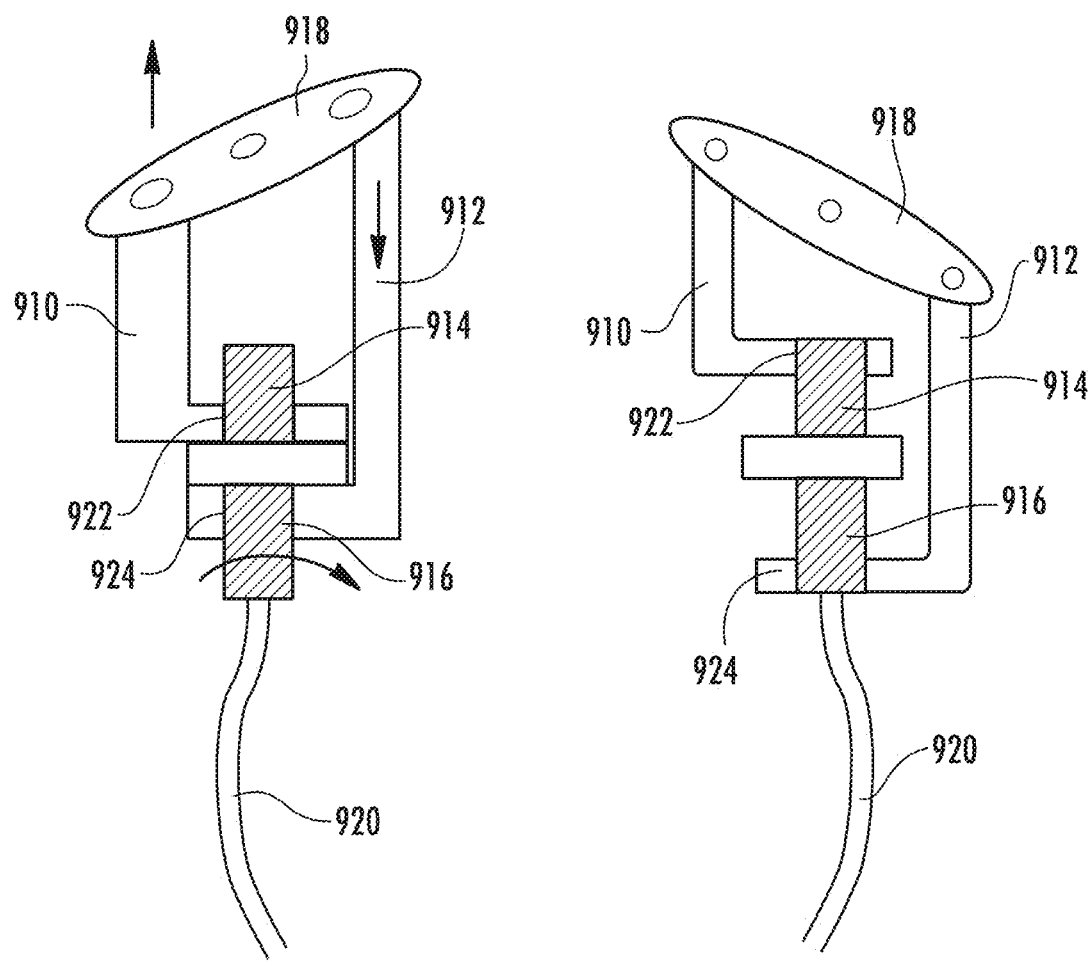
FIG. 36 is a perspective view of another example mechanical esophageal displacement system in accordance with the present disclosure.

FIG. 36 is a perspective view of another example mechanical esophageal displacement system in accordance with the present disclosure. The mechanical esophageal displacement system of FIG. 36 includes an esophageal displacement device that provides articulation via shafts 910, 912, a right-hand threaded rod 914, and a left-hand threaded rod 916, wherein the right-hand threaded rod 914 and a left-hand threaded rod 916 are coupled together axially. When a cable 920 connected to the left-hand threaded rod is rotated, threaded openings 922, 924 in shafts 910, 912, respectively, are moved up and down the threaded rods 914, 916, tilting an articulation plate 918 hingedly connected to the opposite ends of the shafts 910, 912.

Figure 37:
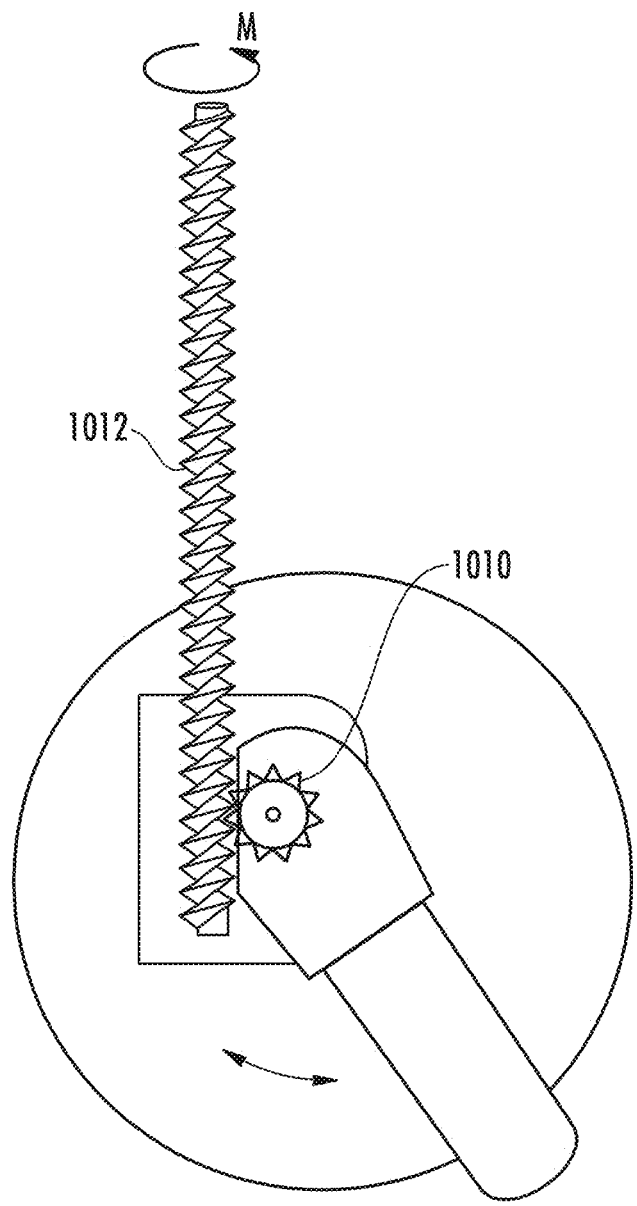
FIG. 37 is a perspective view of another example mechanical esophageal displacement system in accordance with the present disclosure.

FIG. 37 is a perspective view of another example mechanical esophageal displacement system in accordance with the present disclosure. The mechanical esophageal displacement system of FIG. 37 includes a gear drive 1010 that provides articulation via a worm gear 1012.

Figure 38:
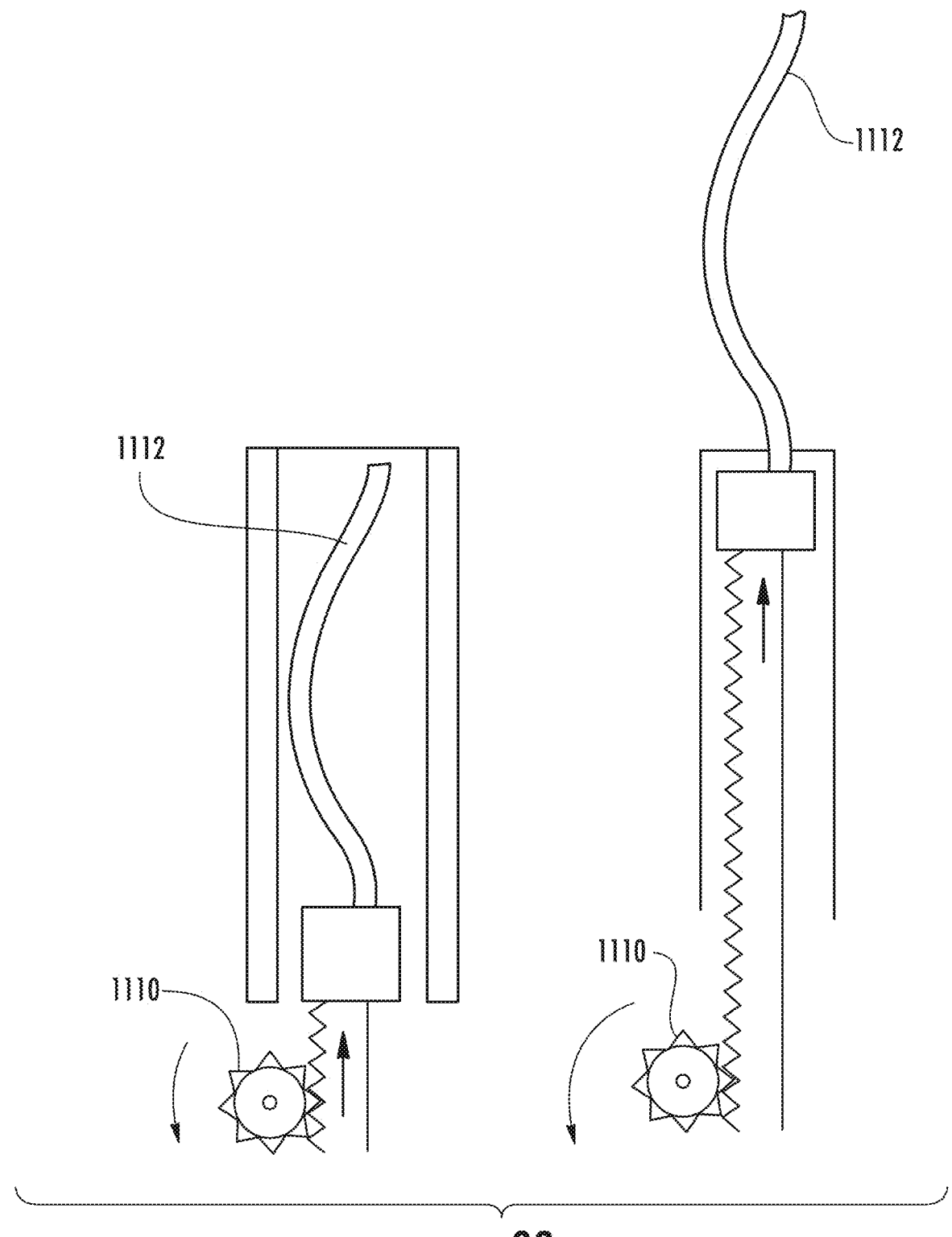
FIG. 38 is a perspective view of another example mechanical esophageal displacement system in accordance with the present disclosure.

FIG. 38 is a perspective view of another example mechanical esophageal displacement system in accordance with the present disclosure. The mechanical esophageal displacement system of FIG. 38 includes a gear drive 1110 that provides articulation via a leaf spring 1112.

Figure 39:
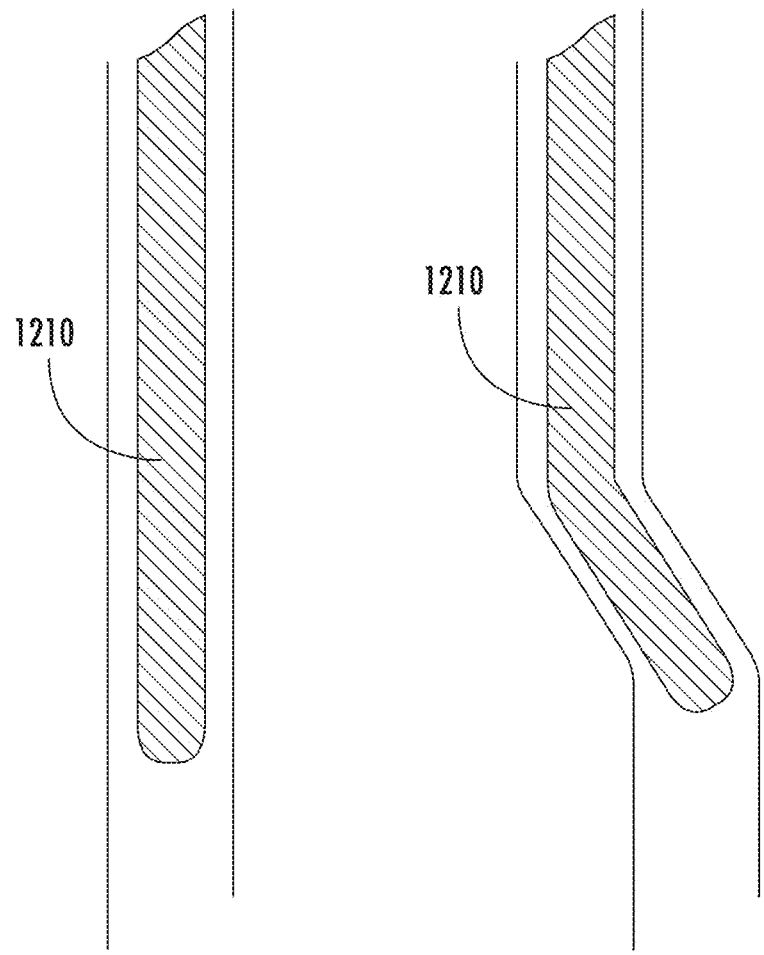
FIG. 39 is a perspective view of another example assembly in accordance with the present disclosure.

FIG. 39 is a perspective view of another example assembly in accordance with the present disclosure. In FIG. 39, the assembly includes an outer tube 1210, similar to outer tube 125, made of a material that deforms to a particular shape when wet.

Figure 40:
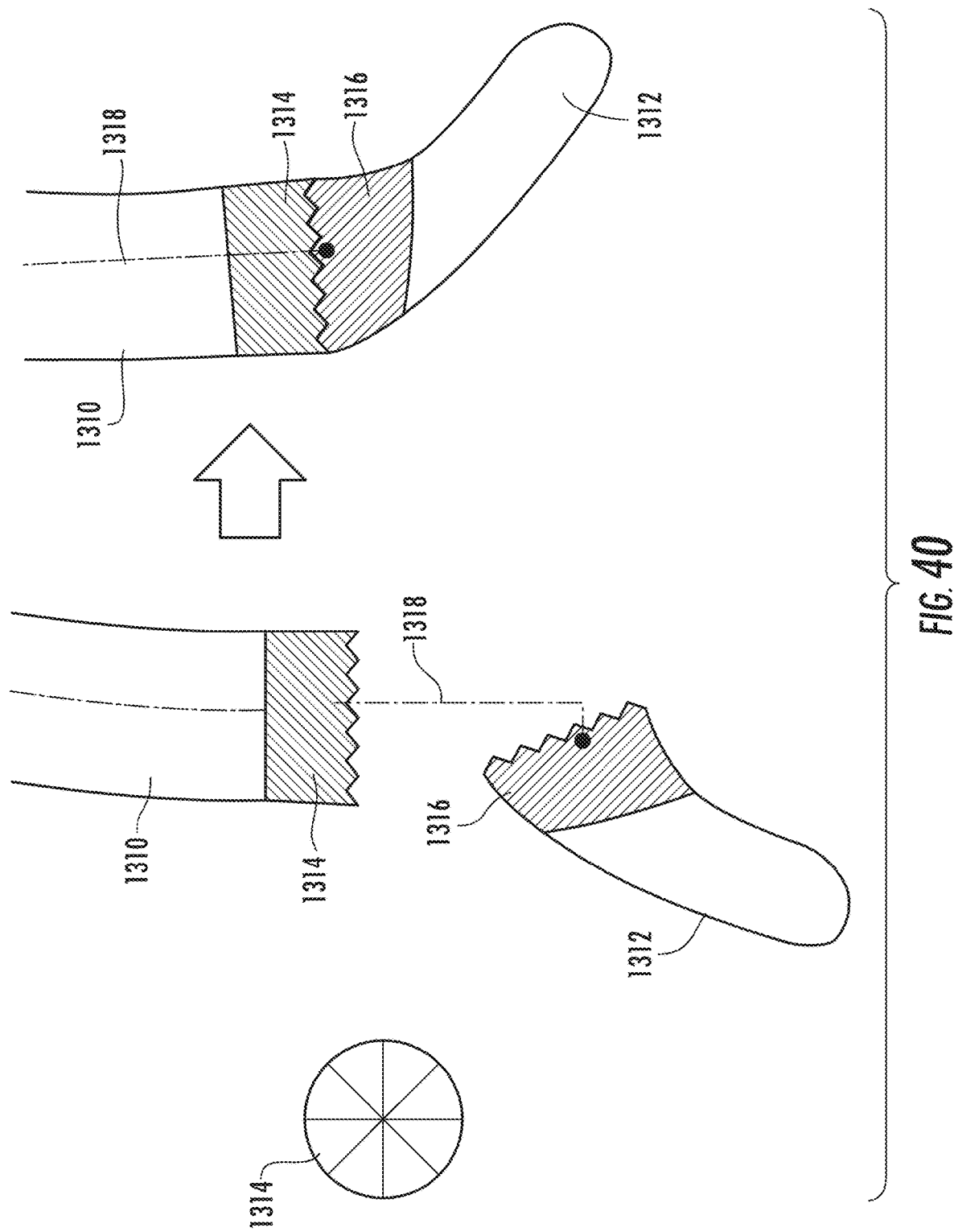
FIG. 40 is a perspective view of another example mechanical esophageal displacement system in accordance with the present disclosure.

FIG. 40 is a perspective view of another example mechanical esophageal displacement system in accordance with the present disclosure. The mechanical esophageal displacement system of FIG. 40 includes a top 1310 and bottom section 1312 that are matched together via a set of axial ridges 1314, 1316, respectively, in which the axial ridges 1314, 1316 prevent rotation. The top 1310 and bottom sections 1312 are connected loosely via a wire 1318. The bottom section 1312 is locked into place when the wire 1318 is pulled up.

Figure 41:
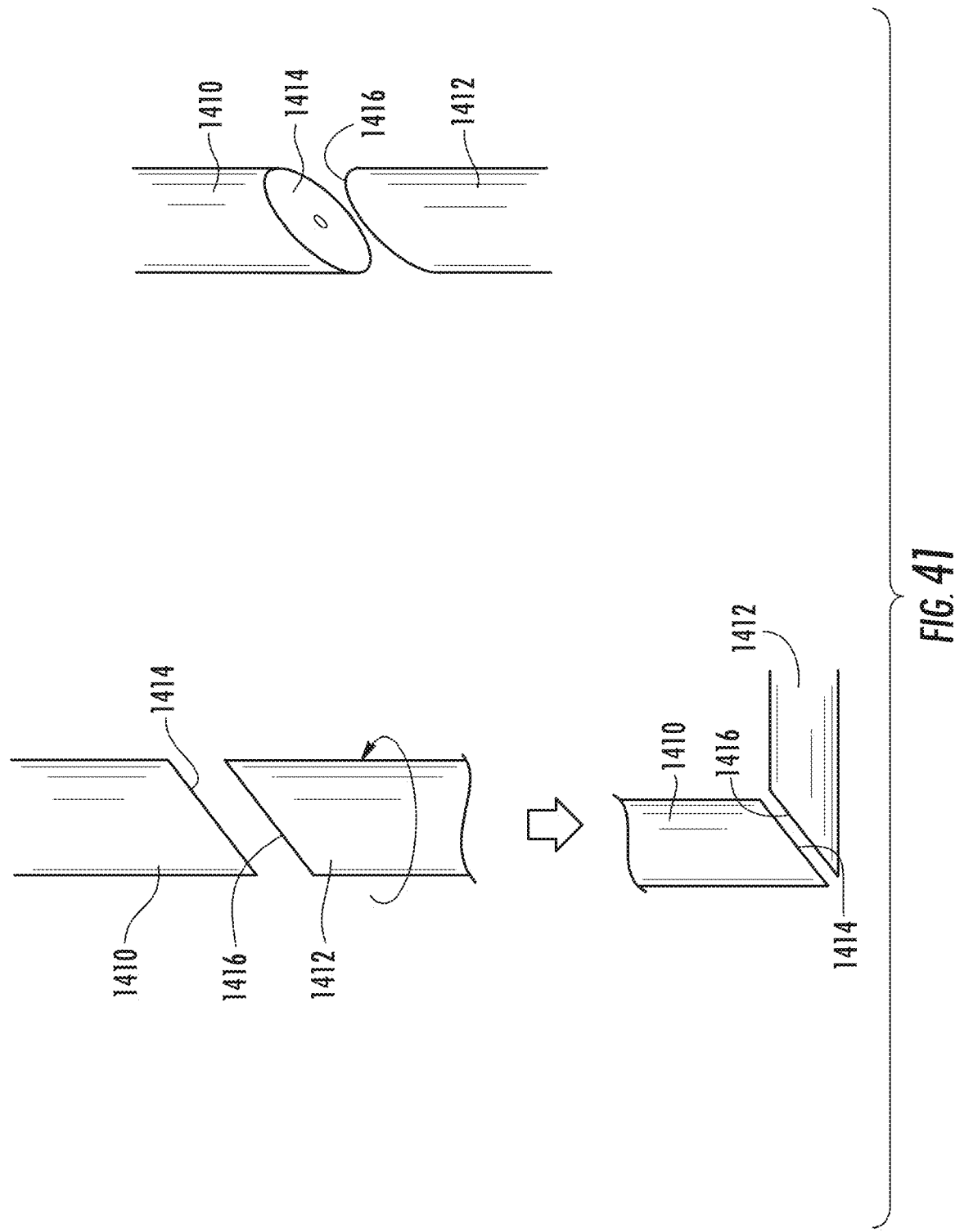
FIG. 41 is a perspective view of another example mechanical esophageal displacement system in accordance with the present disclosure.

FIG. 41 is a perspective view of another example mechanical esophageal displacement system in accordance with the present disclosure. The mechanical esophageal displacement system of FIG. 40 includes an esophageal displacement device having two pieces 1410, 1412 having angled faces 1414, 1416, respectively, in which the angle between of the two pieces 1410, 1412, changes from being aligned to being perpendicular upon rotation.

FIG. 42 is a perspective view of another example assembly in accordance with the present disclosure. The assembly of FIG. 42 includes a straw like tube 1510 that has a flexible portion 1512 only on one side 1514, thus the vacuum when applied causes the one side 1514 of the assembly to deflect.

FIG. 43 is a perspective view of another example assembly in accordance with the present disclosure. The assembly of FIG. 43 includes a gel liquid portion 1610 that causes the assembly to deflect in a given direction.

While some of the means for deflecting the assembly have been described above, it should be noted that the assembly can also be articulated using any other mean known in the art, including, for example, spring, fluid/air-filled container, magnets, etc.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein.

What is claimed is:

1. An assembly for use with a vacuum system comprising:
    a handle;
    a first segment coupled to the handle;
    a second segment connected to the first segment via an articulation pivot pin, the second segment defining a second segment proximal end coupled to the articulation pivot pin and a second segment distal end, the second segment defining a constant length and shape between the second segment distal end and the second segment proximal end;
    an articulation drive cable that pivots the second segment about the first segment; and
    an introducer including a soft outer tube sized to pass through a mouth or nasal passage into an esophagus, the soft outer tube defining a plurality of radial vacuum holes configured to apply a vacuum to an esophageal wall via the vacuum system.

2. The assembly of claim 1, further comprising a tube tip positioned on a distal end of the soft outer tube, the tube tip comprises a hard polymer tip having a soft, circular contour, wherein the tube tip is bonded to the distal end of the soft outer tube.

3. The assembly of claim 1, wherein the introducer further includes a vacuum port comprising a vacuum port body and a vacuum port cap,
    wherein the vacuum port body comprises a vacuum line hook up that is in fluid communication with one or more internal vacuum passages,
    wherein the vacuum port body is bonded to both the introducer and the vacuum port cap to create an air tight seal.

4. The assembly of claim 3, wherein the vacuum port body further includes a vacuum port valve and a lever, wherein the lever controls the vacuum system.

5. The assembly of claim 3, wherein the vacuum port cap includes a hard polymer cap that is bonded to the vacuum port body to selectively couple the handle to the soft outer tube.

6. The assembly of claim 1,
    wherein the introducer further comprises a plurality of radiopaque markers positioned adjacent to the articulation pivot pin,
    wherein the plurality of radiopaque markers span distally to a tube tip.

7. The assembly of claim 1, wherein the plurality of radial vacuum holes are positioned adjacent to the second segment.

8. The assembly of claim 1, wherein the soft outer tube comprises a multi-durometer material such that a stiffness of the soft outer tube varies along a length of the soft outer tube.

9. The assembly of claim 1, further comprising a feedback mechanism to indicate a degree to which a vacuum seal has been formed between the assembly and the esophageal wall.

10. A mechanical esophageal displacement system comprising:
a outer tube defining a plurality of vacuum holes spaced circumferentially around the outer tube and an internal vacuum passage in fluid communication with the plurality of vacuum holes to apply a vacuum to an esophageal wall;
a tube tip located at a distal end of the outer tube; and
an esophageal positioning device sized to be received within the outer tube, the esophageal positioning device including:
a handle;
a first segment coupled to the handle;
a second segment pivotally connected to the first segment via an articulation pivot pin; and
an articulation drive cable that pivots the second segment about the first segment upon actuation between a first position and a second position,
wherein the first segment has a central axis and the second segment has a distal end,
wherein the distal end of the second segment is disposed along the central axis in the first position and the distal end of the second segment is displaced from the central axis in the second position, and
wherein the distal end of the second segment remains a same distance from the articulation pivot pin in the first position and the second position.

11. The mechanical esophageal displacement system of claim 10, wherein the second segment is sized to displace the esophageal wall by about 4 centimeters upon articulation.

12. The mechanical esophageal displacement system of claim 10, wherein the tube tip comprises a hard polymer tip having a soft, circular contour, and
wherein the tube tip is bonded to the distal end of the outer tube.

13. The mechanical esophageal displacement system of claim 10, wherein the outer tube further includes a vacuum port comprising a vacuum port body and a vacuum port cap,
wherein the vacuum port body comprises a vacuum line hook up that is in fluid communication with an internal vacuum passage,
wherein the vacuum port body is bonded to both the outer tube and the vacuum port cap to create an air tight seal.

14. The mechanical esophageal displacement system of claim 13, wherein the vacuum port body further includes a vacuum port valve and a lever,
wherein the lever is configured to control a vacuum system.

15. The mechanical esophageal displacement system of claim 13, wherein the vacuum port cap includes a hard polymer cap that is bonded to the vacuum port body to selectively couple a handle of the esophageal positioning device to a proximal end of the outer tube.

16. The mechanical esophageal displacement system of claim 10,
wherein the outer tube further includes a plurality of radiopaque markers positioned adjacent the articulation pivot pin, and
wherein the plurality of radiopaque markers span distally to the tube tip.

17. The mechanical esophageal displacement system of claim 10, wherein at least one of the plurality of vacuum holes is positioned adjacent the second segment.

18. The mechanical esophageal displacement system of claim 10, wherein the second segment comprises
a distal band laminate assembly,
a distal band guard, and
a distal pivot retainer,
wherein the distal band laminate assembly houses a plurality of distal bands in which all but one of the bands has a slot at a distal end of the plurality of distal bands,
wherein the one band has a hole rather than a slot at the distal end,
wherein the distal band guard retains the distal band laminate assembly by a pin that passes through the plurality of distal bands, and wherein the distal band guard has a rounded tip.

19. The mechanical esophageal displacement system of claim 18, wherein the first segment comprises
a proximal pivot retainer an articulation drive cable, an
a proximal band laminate assembly comprising a plurality of proximal bands,
wherein the proximal pivot retainer houses the proximal band laminate assembly,
wherein the proximal pivot retainer limits the distal pivot retainer from articulating more than 45 degrees to each side to prevent risk of damage to the esophageal wall due to excessive translation.

20. The mechanical esophageal displacement system of claim 19,
wherein the articulation pivot pin connects both the distal pivot retainer and the proximal pivot retainer and allows them to pivot.

\* \* \* \* \*